(12) United States Patent
Hirafuji

(10) Patent No.: US 11,033,675 B2
(45) Date of Patent: Jun. 15, 2021

(54) PORTABLE COMPACT INFUSION DEVICE

(71) Applicant: atDose Co., Ltd., Yokohama (JP)

(72) Inventor: Mamoru Hirafuji, Kawasaki (JP)

(73) Assignee: ATDOSE CO., LTD., Yokohama (JP)

( * ) Notice: Subject to any disclaimer, the term of this patent is extended or adjusted under 35 U.S.C. 154(b) by 0 days.

(21) Appl. No.: 16/605,159

(22) PCT Filed: Apr. 17, 2018

(86) PCT No.: PCT/JP2018/015779
§ 371 (c)(1),
(2) Date: Oct. 14, 2019

(87) PCT Pub. No.: WO2018/194041
PCT Pub. Date: Oct. 25, 2018

(65) Prior Publication Data
US 2021/0100948 A1    Apr. 8, 2021

(30) Foreign Application Priority Data
Apr. 21, 2017  (JP) .............................. JP2017-084081

(51) Int. Cl.
*A61M 5/142*    (2006.01)
*A61M 5/158*    (2006.01)
*A61M 5/168*    (2006.01)

(52) U.S. Cl.
CPC ............ *A61M 5/142* (2013.01); *A61M 5/158* (2013.01); *A61M 5/16886* (2013.01); *A61M 2205/0233* (2013.01); *A61M 2206/20* (2013.01)

(58) Field of Classification Search
CPC .......... A61M 5/142; A61M 2205/0233; A61M 2206/20; A61M 5/158; A61M 5/16886;
(Continued)

(56) References Cited

U.S. PATENT DOCUMENTS

| 2005/0247558 A1* | 11/2005 | Anex ................ A61M 5/14276 204/275.1 |
| 2011/0171626 A1* | 7/2011 | Hirasawa ............... A61K 41/17 435/1.2 |
| 2016/0252082 A1* | 9/2016 | Okumura ................ F04B 19/04 417/48 |

FOREIGN PATENT DOCUMENTS

| EP | 2335710 A1 | 6/2011 |
| JP | 4646976 B2 | 3/2011 |

(Continued)

OTHER PUBLICATIONS

International Search Report dated Jul. 24, 2018 for corresponding international application No. PCT/JP2018/015779 filed Apr. 17, 2018.

(Continued)

*Primary Examiner* — Jason E Flick
(74) *Attorney, Agent, or Firm* — Westman, Champlin & Koehler, PA.; Z. Peter Sawicki; Amanda M. Prose

(57) ABSTRACT

A compact infusion device that is easily portable and inexpensive, can be used safely, and can provide a technique alternative to intravenous drip. The portable compact infusion device includes a fluid drive, a fluid holding portion, a drug solution holding channel, and a support, wherein the fluid drive includes a porous body that allows generation of electroosmotic flow and a pair of rubber electrodes each containing electroconductive material and having a communicating portion, the porous body being sandwiched between the communicating portions of the pair of rubber electrodes to form a sandwiched structure.

10 Claims, 6 Drawing Sheets

(58) Field of Classification Search
CPC ...... A61M 5/00; A61M 5/14; A61M 5/14244; A61M 5/168
See application file for complete search history.

(56) References Cited

FOREIGN PATENT DOCUMENTS

| WO | 2005/113419 A2 | 12/2005 |
|----|----------------|---------|
| WO | 2010/026764 A1 | 3/2010  |
| WO | 2015/059766 A1 | 4/2015  |

OTHER PUBLICATIONS

Written Opinion of the International Searching Authority dated Jul. 24, 2018 for corresponding international application No. PCT/JP2018/015779 filed Apr. 17, 2018.

* cited by examiner

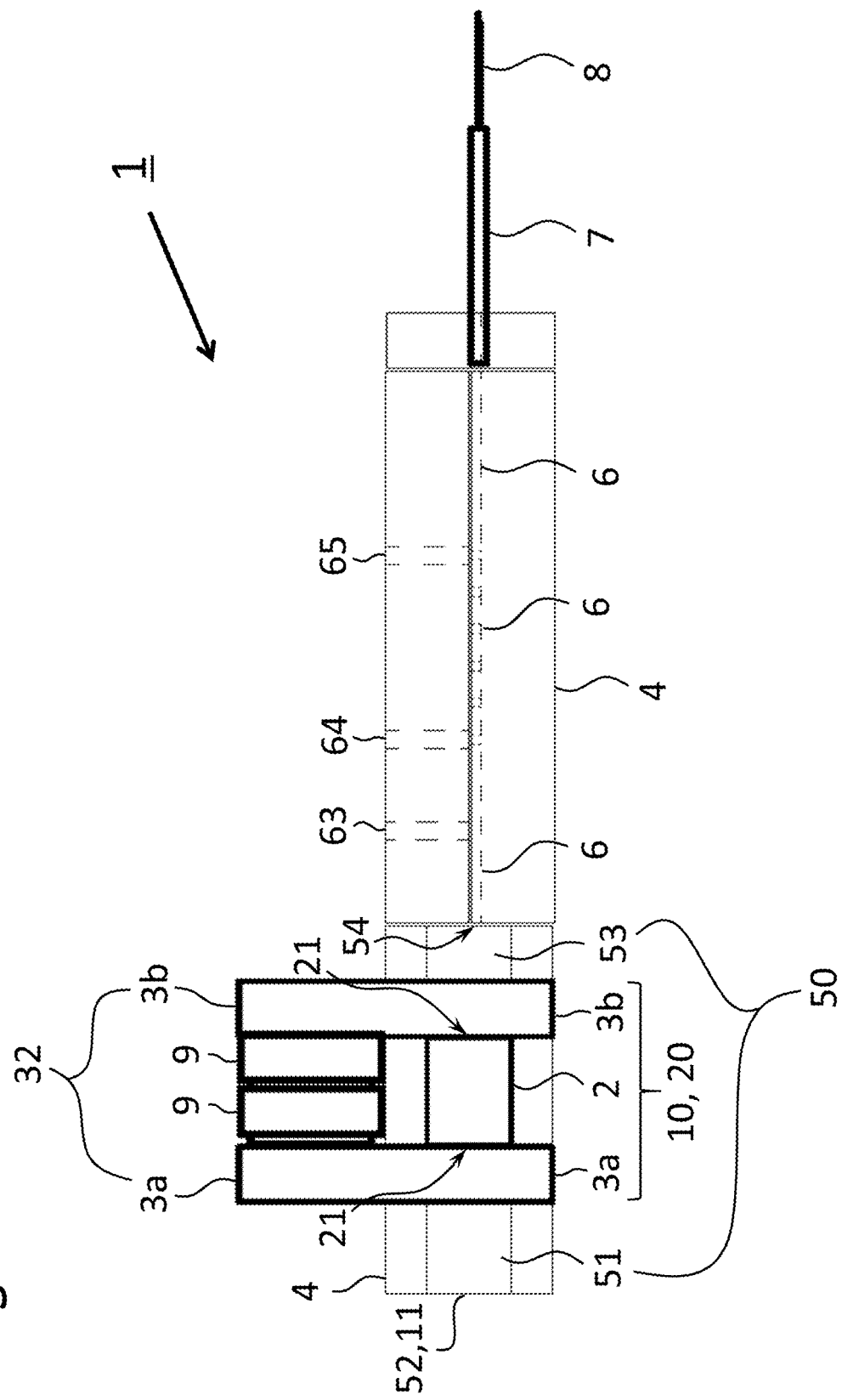

PORTABLE COMPACT INFUSION DEVICE

CROSS-REFERENCE TO RELATED APPLICATION

This application is a Section 371 National Stage Application of International Application No. PCT/JP2018/015779, filed Apr. 17, 2018 and published as WO/2018/194041 on Oct. 25, 2018, in Japanese, the contents of which are hereby incorporated by reference in their entirety.

TECHNICAL FIELD

The present invention relates to a portable compact infusion device. More particularly, it relates to a compact infusion device that is easily portable and inexpensive, can be used safely, and can provide a technique alternative to intravenous drip.

BACKGROUND ART

Intravenous drip (hereinafter, may be referred to as "IV infusion") is a method for intravenously administering medication to the human or animal body and enables to slowly and gradually introduce medicine into the vein. Intravenous drip is widely used in the medical field, because the risk of sudden increase of the drug concentration in the blood can be avoided though the medication is administered to the whole body, and moreover, the intravenous drip can be performed with a device having simple components. Intravenous drip is especially effective for such purposes as administering medicine which may cause anaphylactic shock when administered by injection or the like, or continuously administering medicine whose concentration in the blood needs to be maintained.

In a simple IV infusion method widely and conventionally used in the medical field, an IV bag containing drug solution is hung on the IV pole or the like, the flow rate of the drug solution naturally dropping through the tube is regulated at the portion tightened by a clamp or the like, and the drug is slowly administered through the injection needle, the catheter, or the like inserted into the vein of the patient. In this method, a drip chamber is disposed at a part of a tube or the like through which the drug solution drops from the IV bag, such as a soft resin bag, containing the drug solution. Consequently, the air bubbles are removed as the drug solution drops downward in the drip chamber, and at the same time, the flow rate can be regulated by measuring the number of drops.

An example of the technique for regulating the rate of IV infusion includes a drip-control type infusion device. An example thereof is a device provided with a clamp structure, in which a light sensor is provided at the chamber structure between IV tubes, the number of drops are measured, the infusion rate is regulated by automatically adjusting the clamping force of the clamp applied to the tube, and the device is automatically stopped when the infusion volume reaches the predetermined level.

An example of the technique for more accurately regulating the rate and volume of infusion is the flow control technique in which the solution is transported by an electric motor. Examples of such technique widely used in the medical field include the finger-type infusion pump by which the drug solution is transported through the tube controlled by the motor-operated parts called fingers, and the roller-type infusion pump in which the drug solution is transported through the tube clamped by motor-controlled rollers.

However, in the conventional technique related to the infusion device widely used in the medical field today, the minimum controllable infusion rate is limited, and even though a motor-controlled pump can finely control the infusion rate, the minimum limit of the controllable infusion rate is several tens to a hundred microliters per minute ($\mu$L/min). When a medication is administered in the IV infusion, the drug concentration in the blood needs to be adjusted to a safe level, and thus, the drug needs to be diluted with a large amount of water. Consequently, when the device as described above is used at medical facilities or the like, infusion bags such as bags or bottles having a capacity of several tens to several hundreds of milliliters are needed. Inevitably, the size of the infusion device becomes large, and as a result, various problems occur in reality at medical facilities or the like.

One of the issues to be improved in the medical field is the quality of life of the patients under medication. A patient undergoing infusion therapy is required to be connected to the infusion tube for long hours, and the free movement of the patient is greatly restricted. Another issue from a different viewpoint is the burden placed on medical workers. They are required to be always cautious about the possible dangers involving the infusion device or the infusion tubes when they transport or examine the patient, perform an operation, and so forth. As a result, the doctors and nurses are facing increased burden to prevent medical accidents.

Moreover, the price of the device itself tends to be high because of the motor structure, the control apparatus, or the like of the infusion device, and it should be admitted that today's infusion device has not been used widely by all the patients who need administration of infusion medication in everyday life including those at small clinics and the like.

CITATION LIST

Patent Documents

Patent Document 1: Japanese Patent No. 4646976

SUMMARY OF INVENTION

Technical Problem

The present invention has been achieved in light of the aforementioned circumstances of the conventional techniques, and it is an object thereof to provide a compact infusion device that is easily portable and inexpensive, can be used safely, and can provide a technique alternative to intravenous drip.

Solution to Problem

As a result of intensive study to solve the problems described above, the inventor of the present invention has found that the concentration of the infusion drug can be greatly increased and an infusion device having a compact drug solution reservoir with a capacity of several ten microliters to several milliliters can be obtained when the electroosmotic pump, which can transport a very small amount of liquid at the nanoliter level, whose drive is compact, and which has excellent power consumption efficiency, is employed as the fluid delivery means of the infusion device. The present inventor has found that the problems involving the infusion device described above in the medical field can be solved by developing these findings.

Patent Document 1 discloses the technique related to the conventional infusion device using the electroosmotic flow pump. However, the feature of Patent Document 1 is the electrostatic capacity of the porous body, which serves as the fluid delivery means, and in possible embodiments, such components as the electrode structure and the housing that constitute the device are those obtained by ordinary techniques (see FIG. 12 of Patent Document 1, for example), and many structural members such as O-rings are needed to prevent leakage.

It is a general knowledge in this technical field that the leakage caused by the infusion device poses a serious problem in ensuring the protection of the power source and the safety of the patient. Especially, since a portable compact infusion device is supposed to be carried by the patient, if the device has many connecting portions between members, leakage at any part of these connecting portions may cause fatal accidents.

In order to completely eliminate the risk of contamination or infection caused by the compact infusion device, it is not favorable to reuse the drive including the porous body that has absorbed the used liquid, and it is desirable that the entire device is disposable. However, the device disclosed in Patent Document 1 has such precision structures as the fluid drive and the electrodes, and it should be admitted that this device is not enough suitable for disposable use.

In view of the problems as described above, it should be admitted that the technique disclosed by Patent Document 1 does not fully solve the problem underlying the present invention. The problem cannot be solved even if an electroosmotic flow pump of an ordinary structure is used instead of the electroosmotic flow pump of Patent Document 1, and it is one of the main reasons why the infusion device utilizing the electroosmotic flow pump is not widely used in the medical field.

The present inventor conducted further intensive study under such circumstances and conceived the idea of employing a pair of rubber electrodes containing electroconductive material, each electrode having a communicating portion, so that the porous body can be directly sandwiched by the communicating portions of the rubber electrodes.

The present inventor produced a compact infusion device which had a channel structure formed at the downstream side of the sandwiched structure of the porous body and in which a channel structure for holding the drug solution and the injection needle were connected in series. Then, the present inventor found that the fluid could be delivered moving inside the communicating portions, at which the rubber electrodes communicated with each other through the porous body, and, just by using a structural body obtained by the assembly of very simple members, the fluid driving force could be transmitted toward the downstream channel at flow rates of 1 to 50 nL/min.

The present inventor has found that, by employing the sandwiched structure in which the porous body is sandwiched between the electrodes, i) the fluid drive that functions as a micropump can be obtained just by the combination of simple component members made of inexpensive material, without additionally using sealing members or members for holding the power supply. That is, in this device, leakage can be prevented without using such sealing members as an O-ring. Moreover, the present inventor has found that, in this device, the power supply can be stably held and used just by directly inserting the small batteries between the pair of rubber electrodes containing electroconductive material.

The present inventor has also found that the device according to the present invention having the structure above is a device ii) that is remarkably suitable for disposable use because of its high disposability and easy manufacturability.

Specifically, the present inventor has found that the electrode and the power supply support portion of each electrode can be formed integrally by a rubber member, thereby realizing a device structure that can be disassembled easily at the time of disposal. Moreover, the present inventor has found that the production process of the device can be simplified because the device is made of inexpensive material, has few component members, and has an extremely simple structure. The manufacturing cost of the device is estimated to be reduced to a fraction of the manufacturing cost of the device illustrated in FIG. 12 of Patent Document 1, for example.

It should be noted that a portable compact infusion device which is inexpensive and disposable has yet to come into wide use in the medical field in general at the time of the filing of this application.

The present inventor has also found that the compact infusion device can be remarkably light in weight (e.g. 10 g or less) and extremely portable, because the entire structure of the device is very simple and compact. In contrast, it should be admitted that the conventional device illustrated in FIG. 12 of Patent Document 1, which is estimated to have a weight of at least about several ten to one hundred grams, does not have good portability when its device structure is compared with that of the present invention.

Based on these findings, the present inventor has accomplished the present invention. The present invention specifically relates to aspects of the invention described below.

[1] A portable compact infusion device including:
a fluid drive;
a fluid holding portion;
a drug solution holding channel; and
a support,
wherein (A) the fluid drive includes a porous body that allows generation of electroosmotic flow and a pair of rubber electrodes each containing electroconductive material and having a communicating portion, the porous body being sandwiched between the communicating portions of the pair of rubber electrodes to form a sandwiched structure;

(B) the fluid holding portion includes a fluid supply reservoir spatially in contact with the communicating portion of one of the rubber electrodes in the sandwiched structure or connected to the communicating portion of the one of the rubber electrodes in the sandwiched structure through a member having a space or a channel; and (C) the drug solution holding channel is spatially in contact with the communicating portion of the other rubber electrode in the sandwiched structure or is connected to the communicating portion of the other rubber electrode in the sandwiched structure through a member having a space or a channel, and a part of the drug solution holding channel is directly or indirectly connectable to an injection needle.

[2] The compact infusion device of aspect 1,
wherein (A') the fluid drive is operable as an electroosmotic flow pump; and
(B') the fluid holding portion is a container-like structure/structures to hold fluid.

[3] The compact infusion device of aspect 1 or 2, wherein in the fluid drive, (a-1) the communicating portions of the pair of rubber electrodes in the sandwiched structure are substantially opposed to each other and sandwich the porous body in a manner in contact with the porous body;

(a-2) the porous body is embedded in the support with a space provided at one side of each rubber electrode opposite to the porous body with respect to the communicating portion of each rubber electrode in the sandwiched structure; and (a-3) each of the rubber electrodes includes a protruding portion that protrudes from the support, and the protruding portions of the rubber electrodes are positioned to directly hold small batteries between the rubber electrodes.

[4] The compact infusion device of any one of aspects 1 to 3, wherein the communicating portion of each rubber electrode includes a communicating hole, and the sandwiched structure includes a peripheral edge of the communicating hole of each rubber electrode partially or entirely in contact with the porous body.

[5] The compact infusion device of any one of aspects 1 to 4, wherein the fluid drive generates a driving force that transports the fluid at a position nearer the fluid supply reservoir than the pair of rubber electrodes toward a position nearer the drug solution holding channel than the pair of rubber electrodes;

the driving force is transmitted to transport a drug solution held inside the drug solution holding channel toward the injection needle; and infusion through the injection needle is performed without pulsation at flow rates of 1 to 50 nL/min.

[6] The compact infusion device of any one of aspects 1 to 5, wherein at least parts of the support in contact with the rubber electrodes are made of resin or rubber material.

[7] The compact infusion device of any one of aspects 1 to 6, wherein the drug solution holding channel is substantially composed of a fine channel having a maximum channel width of 1 mm or less, and is configured to hold a drug solution of 0.01 to 4 mL.

[8] The compact infusion device of any one of aspects 1 to 7, including the injection needle connected to or connectable to the compact infusion device.

[9] The compact infusion device of any one of aspects 1 to 8, wherein the porous body is immersed in the fluid, and the fluid holding portion contains the fluid.

[10] The compact infusion device of any one of aspects 1 to 9, wherein the total weight of the fluid drive, the fluid holding portion, the drug solution holding channel, and the support is 10 g or less.

Advantageous Effects of Invention

The present invention can provide a compact infusion device that is easily portable and inexpensive, can be used safely, and can provide a technique alternative to intravenous drip.

For example, the compact infusion device according to the present invention enables to intravenously administer a very small amount of medication for long hours and is expected to be used as an alternative technique for intravenous drip in the medical field because the device has a size and weight suitable for portable use. Moreover, since the device according to the present invention enables to perform infusion at a very low flow rate, it becomes possible to administer subcutaneous injection of a very small amount of medication continuously for long hours, directly into the affected part.

In the present disclosure, the structure for preventing leakage can be realized by extremely simple composition of members. Therefore, for example, it becomes possible to provide an inexpensive, highly disposable compact infusion device, which has not been obtained by conventional techniques. As a result, the device according to the present invention is expected to help prevent the risk of contamination, infection, and the like.

Since the entire structure of the device according to the present invention is extremely simple and compact, it becomes even possible to provide a remarkably portable compact infusion device having a weight of 10 g or less.

BRIEF DESCRIPTION OF DRAWINGS

FIG. 2 illustrates a side view of the structure of the compact infusion device according to one embodiment of the present invention, as viewed from the long side of the support. The dashed lines indicate the structure that cannot be directly seen in this view.

FIG. 3A illustrates a side view of the downstream rubber plate electrode being inserted into and fixed to the support, as viewed from the direction of the opening of the fluid supply reservoir. FIG. 3B illustrates the back view of the rubber plate electrode. FIG. 3C illustrates the side view of the rubber plate electrode.

FIG. 5A shows the weight of the device before inserting the button cells. FIG. 5B shows the weight of the device after inserting the button cells.

FIG. 6A shows the weight of the device before inserting the button cells. FIG. 6B shows the weight of the device after inserting the button cells.

DESCRIPTION OF EMBODIMENTS

Figure 1:
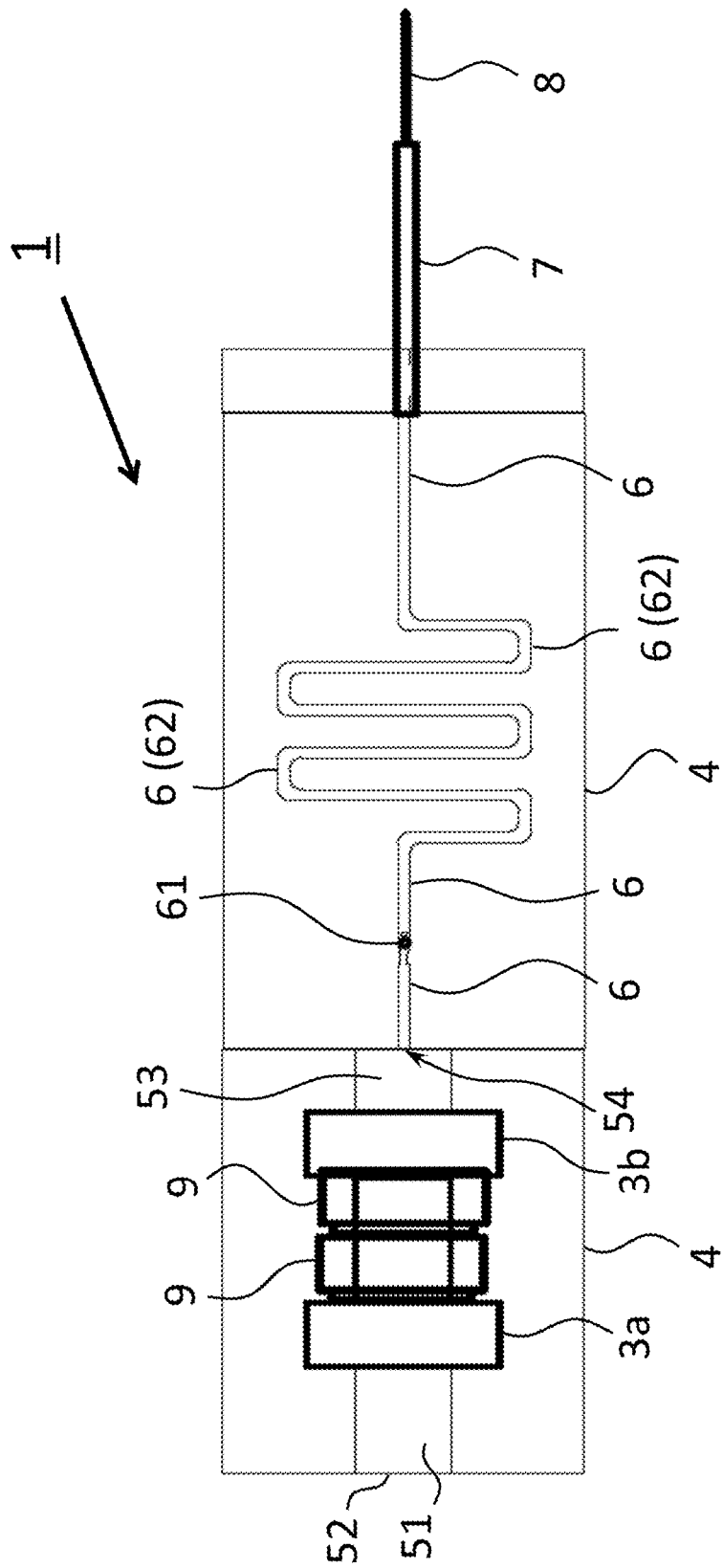
FIG. 1 illustrates a top view of the structure of the compact infusion device according to one embodiment of the present invention.
Figure 3A:
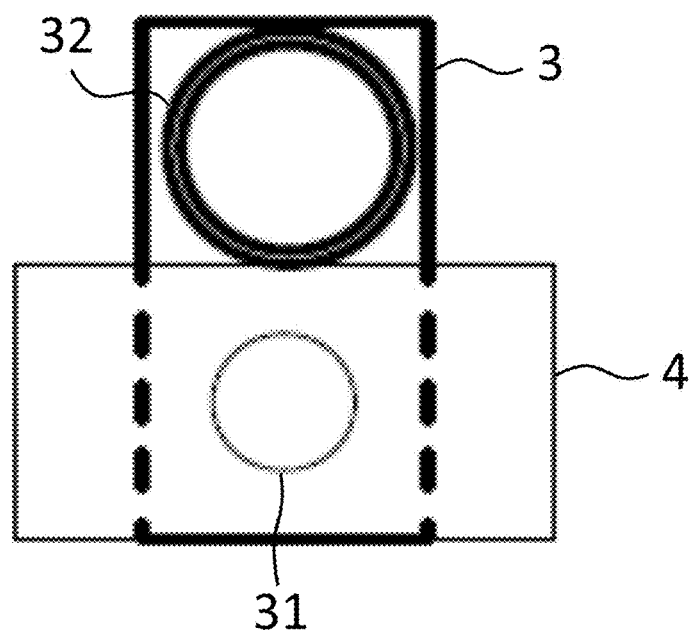
FIGS. 3A-3C illustrate the structure of the rubber plate electrode during the production process of the compact infusion device according to the present invention. The dashed lines indicate the structure that cannot be directly seen in this view.
Figure 3B:
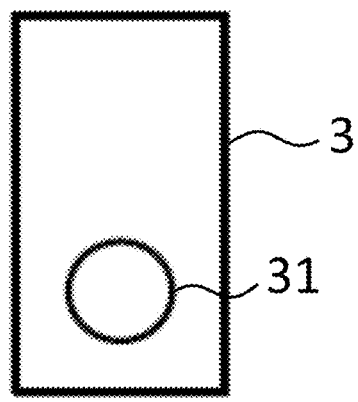
Figure 3C:
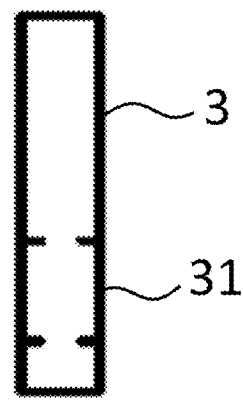
Figure 4:
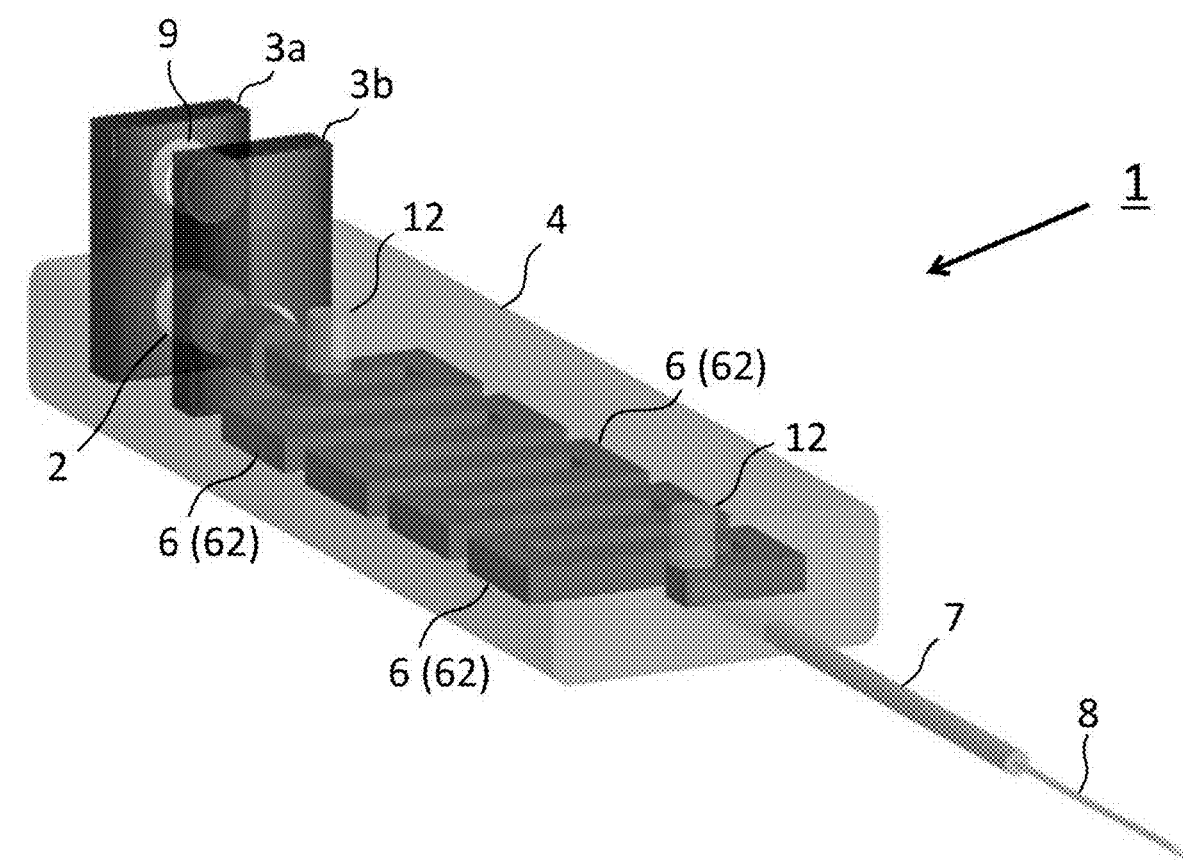
FIG. 4 is a top perspective view showing the entire structure of the compact infusion device according to one embodiment of the present invention.

The present invention relates to a portable compact infusion device. More particularly, it relates to a compact infusion device that is easily portable and inexpensive, can be used safely, and can provide a technique alternative to intravenous drip. Hereinafter, embodiments of the present invention will be described in detail. The reference numerals in the following description refer to those used in the drawings.

The present application claims priority to Japanese Patent Application Serial No. 2017-084081 filed with the Japan Patent Office by the applicant of the present invention, the entire contents of which are incorporated herein by reference.

Terminology

The term "electroosmotic flow phenomenon" as used herein refers to the phenomenon in which, when a voltage is applied to the two different sides of the porous body which has absorbed liquid, the liquid in the porous body moves from one electrode side to the other. The term "electroosmotic flow" as used herein refers to the flow of the liquid generated by this electroosmotic flow phenomenon.

1. Compact Infusion Device

The present invention relates to a compact infusion device 1 that is easily portable and inexpensive, can be used safely, and can provide a technique alternative to intravenous drip. More specifically, the present invention relates to a portable compact infusion device whose components include a fluid drive 10, a fluid holding portion 50, a drug solution holding channel 6, and a support 4, wherein the fluid drive has a sandwiched structure in which the porous body that allows the generation of electroosmotic flow is sandwiched between the communicating portions of the pair of rubber electrodes containing electroconductive material.

The scope of the invention is not limited to the embodiments including all the features described below, especially with regard to the features other than those necessary for the device according to the present invention.

[Fluid Drive]

The component members of the compact infusion device 1 according to the present invention include the fluid drive 10. The fluid drive 10 according to the present invention is operable as an electroosmotic flow pump. That is, it is preferable that the fluid drive 10 is an electroosmotic flow pump.

The fluid drive according to the present invention is a component member i) including the porous body that allows the generation of electroosmotic flow and the pair of rubber electrodes each containing electroconductive material and having the communicating portion, ii) the porous body being sandwiched between the communicating portions of the pair of rubber electrodes to form a sandwiched structure. More preferably, in the fluid drive according to the present invention, the structure described in ii) is formed only by the members described in i).

In the device according to the present invention, the sandwiched structure in the fluid drive makes it possible to efficiently transport the electroosmotic flow generated in the porous body toward the downstream channel side. That is, driven by the liquid driving force generated by the electroosmotic flow pump, the fluid in the fluid supply reservoir 51 passes through the upstream communicating portion (31 of the rubber electrode 3a), through the porous body 2, and through the downstream communicating portion (31 of the rubber electrode 3b), and moves toward the drug solution holding channel 6 side. The movement of the fluid transmits the driving force to induce the downstream movement of the drug solution in the drug solution holding channel.

At the same time, in the device according to the present invention, the features of the sandwiched structure help realize a device structure that can prevent the leakage of liquid and that can achieve a very light weight suitable for portable use though the device is quite simple in composition, and consequently, the entire device can be configured to be disposable in some embodiments.

Porous Body

The porous body 2, which is a component of the fluid drive 10, can be made of material which has adequate strength and which can generate electroosmotic flow inside the porous body when a voltage is applied. Material that can be used for an ordinary electroosmotic flow pump can be used.

The material of the porous body 2 preferably has high dielectricity. A porous body having high dielectricity is preferable because it can efficiently generate electroosmotic flow and the device can be driven continuously for long hours.

The porous body 2 preferably has a fine porous microstructure that allows the movement of the fluid from one side to the other side of the sandwiched structure. It is preferable that the average pore size is 5 μm or less, preferably 2.5 μm or less, more preferably 1 μm or less, and even more preferably 0.5 μm or less so that the fine porous structure may function as a fine channel structure. It is preferable that the average pore size of the fine structure of the porous body is small, because the ratio of the cavity surface area to the volume becomes high and greater electroosmotic flow can be generated. Yet, when the average pore size is too small, the pores may be clogged. Therefore, the lower limit of the average pore size is preferably 0.1 μm or more, for example.

It is desirable that the porous body 2 has an average porosity of 1% or more, preferably 2.5% or more, and more preferably 5% or more. It is preferable that the porous body has a high average porosity, because the ratio of the surface area to the volume becomes high and greater electroosmotic flow can be generated. Yet, when the average porosity is too high, it can cause different problems, such as impairing the strength of the member. Therefore, the upper limit of the average porosity is preferably 50% or less, for example.

Any material having fine porous structure can serve as the material for the porous body 2, and porous material made of ceramic is especially desirable. For example, the material of the ceramic can be alumina, aluminum nitride, silicon nitride, silicon carbide, silicon oxide, or a mixture of two or more selected from the group consisting of these substances. Porous sintered ceramic material is preferable. It is especially preferable to use a material that has high dielectricity and good porosity.

Material in which less air bubbles are produced during the generation of the electroosmotic flow is preferable as the material for the porous body 2. Yet, since a fine channel structure is employed as the drug solution holding channel 6 of the device according to the present invention, even if fine air bubbles are generated during the generation of the electroosmotic flow, the driving force is transmitted by the surface tension at the interface inside the fine channel, and the fine air bubbles generated in the porous body are not transported toward the drug solution. Therefore, it is even possible to select material that may cause the generation of air bubbles as the material for the porous body according to the present invention.

With regard to the shape of the porous body 2, a shape suitable for being sandwiched between the pair of rubber electrodes can be selected appropriately, and a porous body that has a certain cross-sectional area (which ensures a certain flow rate of the fluid) and a certain length of the member (which ensures a certain distance between electrodes) can be employed.

In a preferred embodiment, it is desirable that the shape of the porous body 2 does not prevent the fluid from moving from one electrode to the other. Specifically, it is desirable that the porous body has a practically uniform cross section throughout the entire length in the moving direction of the fluid.

In a preferred embodiment, it is desirable that the porous body has two surfaces 21, one of which comes into contact with one of the pair of rubber electrodes and the other of which comes into contact with the other of the pair of rubber electrodes, and at least the portion of each surface which comes into contact with the respective rubber electrode is planar. Moreover, these two surfaces are preferably parallel to each other.

The shape of the porous body 2 can be obtained by laying lengthwise a cylindrical shape, an oval cylindrical shape, an elliptic cylindrical shape, a polygonal prism shape (a triangular prism, a quadrangular prism, or other polygonal prisms with more sides), a rectangular cuboid shape, a cube shape, or a shape substantially equivalent to these shapes. The shape of the porous body can also be obtained by chamfering the edges of the left and right side surfaces, the upper surface, the bottom surface or the like of these three-dimensional shapes extending lengthwise. It is also possible to employ deformed shapes of these shapes, such as those having regions protruding toward or curved away from the respective holes of the communicating portions 31 of the rubber electrodes.

It is especially preferable that the porous body 2 has a cylindrical shape, a polygonal prism shape, or the like.

The size of the porous body 2 may be appropriately selected depending on embodiments. Yet, in order to generate the electroosmotic flow sufficient for the compact infusion device, it is desirable that the cross-sectional area vertical to the moving direction of the fluid (in the embodiment shown in FIG. 1 and the like, the cross section vertical to the longitudinal direction of the device) is 0.2 mm$^2$ or more, preferably 1 mm$^2$ or more. Since high electric power is required to generate the electroosmotic flow when the cross section is too large, the upper limit of the cross-sectional area is preferably 100 mm$^2$ or less, for example.

Similarly, in order to generate the electroosmotic flow sufficient for the compact infusion device, it is desirable that the length of the porous body (in the embodiment shown in FIG. 1 and the like, the length in the longitudinal direction of the device) sandwiched between the electrodes is 1 mm or more, preferably 3 mm or more. Since the electric field strength (V/cm) weakens due to the longer distance between the electrodes when the length of the porous body is too long, the upper limit of the length can be 20 mm or less, preferably 15 mm or less, for example.

Rubber Electrodes Containing Electroconductive Material

The component members of the fluid drive 10 according to the present invention include the pair of rubber electrodes 3 containing electroconductive material and sandwiching the porous body. The pair of rubber electrodes 3 form an electrode pair and consist of two separate electrode members or more than two separate electrode members. One of the electrodes forming the pair of rubber electrodes is the electrode 3a provided at the fluid supply reservoir side (upstream side) and the other is the electrode 3b provided at the drug solution holding channel side (downstream side).

The rubber electrodes 3 according to the present invention contain electroconductive material and thus are electrically conductive. By adjusting the content of the electroconductive material in the rubber electrodes 3, it becomes possible to control the electroconductivity of the electrodes, the rate of the electroosmotic flow, and consequently, the flow rate of the infusion device.

That is, when the content of the electroconductive material in the rubber electrode 3 is reduced, an infusion device having low electroconductivity and a low flow rate can be manufactured. On the other hand, when the content of the electroconductive material is increased, an infusion device having high electroconductivity and a high flow rate can be manufactured.

The electroconductive material contained in the rubber electrodes can be made of metal such as silver, copper, platinum, stainless steel, and titanium, but it is preferable to use carbon as the electroconductive material. When rubber electrodes containing carbon are employed as the rubber electrodes 3, various advantages can be achieved: for example, less air bubbles are generated along with the generation of electroosmotic flow, the safety of the device improves, and the device can be easily processed during the manufacturing process and have high disposability. That is, it is especially preferable to use rubber electrodes containing carbon as the rubber electrodes according to the present invention.

While the rubber electrodes 3 function as the electrode members having electroconductivity as described above, they also have elasticity and strength, which are the physical properties of rubber. These features of the rubber material of the rubber electrodes help achieve various features, such as the tight contact between the rubber electrode and the support, and the elasticity of the power support portion. As a result, some of the essential features of the compact infusion device according to the present invention can be achieved.

Any ordinary rubber material such as natural rubber or synthetic rubber can be employed without limitation as the rubber material of the rubber electrodes 3. For example, the rubber electrode 3 can be made of natural rubber, isoprene rubber, butadiene rubber, styrene-butadiene rubber, butyl rubber, nitrile rubber, ethylene-propylene rubber, chloroprene rubber, acrylic rubber, chlorosulfonated polyethylene rubber, urethane rubber, silicone rubber, fluorinated rubber, epichlorohydrin rubber, or polysulfide rubber. It is preferable to use silicone rubber or the like to ensure tight contact at the contact portions, the elasticity and strength of the power supply support portion, and the like.

It is preferable that both the pair of rubber electrodes 3 of the device of the present disclosure are made of substantially the same material. Preferably, both the pair of electrodes are made of the same material.

In some possible embodiments, the pair of rubber electrodes 3 may also be made of material different from each other and/or material having different contents of electroconductive material, as long as the functions of the device according to the present invention are not lost.

The rubber electrode 3 according to the present invention is an electrode member having a communicating portion 31 (communicating structure 31). In the fluid drive according to the present invention, a structure in which the porous body 2 is sandwiched between the communicating portions 31 of the pair of rubber electrodes is formed. In this sandwiched structure 20, the fluid moves from the communicating portion on the upper stream side to the communicating portion on the lower stream side as it percolates through (passes through, goes through) the porous body, and consequently, the driving force is transmitted to the channel located further downstream. That is, by the driving force generated by the electroosmotic pump here, the fluid in the fluid supply reservoir 51 moves through the communicating portion on the upper stream side (31 of the rubber electrode 3a), through the porous body 2, and then through the communicating portion on the lower stream side (31 of the rubber electrode 3b), and consequently, is transported to the drug solution holding channel 6 side. The movement of the fluid transmits the driving force that subsequently transports the drug solution in the drug solution holding channel toward the downstream side.

The communicating portions 31 of the rubber electrodes are preferably provided at positions that can ensure the movement of the fluid in the sandwiched structure 20.

In a specific embodiment, the communicating portion 31 may be provided with a hole through which the front and back surfaces of the rubber electrode 3 communicate with each other. That is, in the present invention, the communicating portion 31 can be a structure having a communicating hole. Specifically, a relatively large hole shape can be employed as the communicating hole 31 in order to ensure the generation of the electroosmotic flow sufficient for the compact infusion device.

The communicating hole 31 can have any shape that allows the peripheral edge of the communicating hole to be in contact with the porous body in the sandwiched structure. For example, the communicating hole can have a circular shape, an oval shape, an elliptic shape, a polygonal shape (a triangular shape, a quadrangular shape, or other polygonal shapes with more sides), a rectangular shape, or a shape substantially equivalent to these shapes. A circular shape, a polygonal shape, or the like is especially preferable.

The communicating hole 31 can have any size that allows the peripheral edge of the communicating hole to be partially or entirely, preferably entirely, in contact with one flat side surface of the porous body, and it is desirable that the cross-sectional area of the communicating hole vertical to the moving direction of the fluid (in the embodiment shown in FIG. 1 and the like, the cross section vertical to the longitudinal direction of the device) is 0.2 mm$^2$ or more, preferably 1 mm$^2$ or more, in order to ensure the generation of the electroosmotic flow sufficient for the compact infusion device. Since high electric power is required to generate the electroosmotic flow when the cross section is too large, the upper limit of the cross-sectional area is preferably 100 mm$^2$ or less, for example.

In an embodiment in which only a part of the peripheral edge of the communicating hole is in contact with the flat side surface of the solid shape of the porous body, it is desirable that the portion that is not in contact with the porous body is blocked by the support 4 or the like in order to prevent the fluid from leaking through the gap or the like between members without passing through the porous body.

In another embodiment of the communicating portion 31, it is possible to employ various structures through which the front and back surfaces of the rubber electrode 3 communicate with each other. For example, the communicating portion can be formed into such patterns as a net pattern, a slit pattern, a lattice pattern, or a honeycomb pattern. In still another embodiment, a large communicating portion can be formed as an assembly of a plurality of communicating portions or an assembly of fine pore-like communicating portions.

The communicating portion 31 in these embodiments can have any size that allows the communicating portion to be partially or entirely, preferably entirely, in contact with the flat side surface 21 of the solid shape of the porous body. It is desirable that the total area of the porous portions of the communicating portion falls within the range described above when the generation efficiency of the electroosmotic flow and the like is taken into consideration.

The rubber electrodes 3 preferably have areas that can hold small batteries when the pair of rubber electrodes are disposed to face each other. These areas can serve as the power supply support portions 32 in the device according to the present invention. In a preferred embodiment to achieve this function, the portion located above the communicating portion 31 and protruding outward from the support can be used as the power supply support area, for example.

With regard to the entire shape of the rubber electrode 3, the rubber electrode preferably has a shape suitable for holding the porous body 2 when the pair of rubber electrodes are disposed to face each other. In one example of the shape suitable for achieving this function, when the pair of rubber electrodes are disposed to face each other, the rubber electrodes have flat surfaces facing each other at least at the regions including the communicating portions.

Also, in a preferred embodiment, each power supply support portion 32 for holding small batteries has a flat surface, such that the flat surface of the power supply support portion of one electrode faces that of the other electrode.

In view of such advantages as the reduction of material costs and simplification of the manufacturing process, each electrode member constituting the pair of rubber electrodes 3 preferably has an entirely integrated shape that is provided with necessary functions and structures. It is preferable that a flat shape is employed as the basic shape of the entire electrode and the flat shape is molded to have necessary functions and structures.

In a preferred embodiment, two electrode members are used as the pair of rubber electrodes 3. For example, in some embodiments, as shown in FIG. 1 and the like, the pair electrodes may consist of two electrode members, which are the upstream rubber electrode 3a and the downstream rubber electrode 3a.

With regard to the shape of the rubber electrode 3, the electrode of one polarity can be provided as an assembly of two or more electrode members. In some embodiments, a plurality of electrode members may be engaged or connected to each other, or a plurality of electrode members may be located separately at a distance from each other, for example.

In these embodiments, the communicating portion 31 can be formed by the combination of electrode members of the same polarity. Alternatively, the gap between the electrode members of the same polarity can directly serve as the communicating portion 31.

The size of the rubber electrode 3 may be determined appropriately depending on the embodiments. When the rubber plate electrode as described in the examples section is employed, the vertical height of the rubber electrode can be 5 to 50 mm, for example, in order to have a size suitable for the compact infusion device. The width of the rubber electrode (in the embodiment shown in FIG. 1 and the like, the width vertical to the longitudinal direction of the hollow structure 5) in this embodiment can be any size that allows the rubber electrode to have portions in contact with the porous body and the small batteries, and its example is 3 to 30 mm. The thickness of the rubber electrode (in the embodiment shown in FIG. 1 and the like, the width in the longitudinal direction of the hollow structure 5) in this embodiment can be any size that can provide strength to the electrode, and its example is 0.5 to 20 mm.

The portion of the rubber electrode 3 that is brought into contact with the porous body 2 in the sandwiched structure 20 can have a shape suitable for the contact with the porous body. For example, in one embodiment, the peripheral edge or its surrounding portion of the communicating portion 31 can be provided with a flat surface that comes into contact with the flat side surface 21 of the porous body. In another embodiment, the peripheral edge or its surrounding portion of the communicating portion 31 may be provided with a fitting structure that can be fitted to the peripheral edge of the side surface 21 of the porous body.

The fitting structure can be a recessed structure or the like that can be fitted to the peripheral edge of the porous body. Moreover, the fitting structure is not limited to such a structure, and a different structure can also be employed.

The portion constituting the power supply support portion 32 of the rubber electrode 3 that is brought into contact with the small battery can have a fitting structure having a shape suitable for being fitted to the outer edge of the small battery.

The fitting structure can be a recessed structure that can be fitted to the outer edge of the small battery, a holder structure that can be fitted to the outer side of the small battery, or the like. Moreover, the fitting structure is not limited to such a structure, and a different structure can also be employed.

Sandwiched Structure

The fluid drive 10 according to the present invention is provided with the sandwiched structure 20 in which the porous body is disposed to be sandwiched between the pair of rubber electrodes. The sandwiched structure is the assembly of members functioning as the drive portion of the compact infusion device according to the present invention and is a characteristic feature that contributes to the various effects achieved by the device 1 according to the present invention.

In the sandwiched structure 20, the communicating portions 31 of the pair of rubber electrodes are substantially opposed to each other and sandwich the porous body in a manner in contact with the porous body. Specifically, when the porous body has a three-dimensional shape having two flat side surfaces 21 parallel to each other, the communicating portions 31 are preferably disposed in contact with these surfaces.

It is desirable that, when the communicating portion 31 has a communicating hole, the outer periphery of the communicating hole of the rubber electrode in the sandwiched structure 20 is partially or entirely in contact with the porous body.

When the communicating portions 31 face with each other as described above, the direction of the communicating portions of the pair of rubber electrodes preferably overlap with each other in a substantially horizontal direction when the device is placed horizontally. Though there can be some difference in the positions or the directions of the communicating portions as long as the functions of the device according to the present invention is not practically lost, it is preferable that the communicating portions of the rubber electrodes are disposed in a direction in which the communicating portions precisely face with each other.

The pair of rubber electrodes constituting the sandwiched structure 20 are pair electrodes opposing to each other. One of the electrodes is the electrode 3a provided at the fluid supply reservoir side (upstream side) and the other is the electrode 3b provided at the drug solution holding channel side (downstream side).

The distance between the pair of rubber electrodes is preferably designed to be the shortest distance for holding the side surfaces 21 of the porous body, which can be determined depending on the length of the porous body 2 (in the embodiment shown in FIG. 1 and the like, the length in the longitudinal direction of the device). Specifically, the range of the length of the porous body described above can be referred to and applied upon determining the range of the distance between electrodes.

It is preferable that the pair of rubber electrodes are formed such that the communicating portions of the respective electrodes face with each other and/or the power supply support portions of the respective electrodes face with each other. In some embodiments, the shapes, the materials, or the like of the respective electrodes in the sandwiched structure can be different from each other as long as these rubber electrodes do not practically bring about negative effects on the functions of the device according to the present invention.

In the device according to the present invention, the sandwiched structure formed by the porous body and the electrodes is fixed and supported by the support 4. The porous body 2 is embedded in the support 4. Preferably, the porous body is embedded in the support 4 with a space provided at one side of each rubber electrode opposite to the porous body with respect to the communicating portion of each rubber electrode in the sandwiched structure.

It is preferable that, in the embedded structure, the surfaces of the porous body located between the pair of the electrodes are fixed and supported in the space inside the support in order to prevent the fluid from leaking through the gaps between members or the like without passing through the porous body. A fixing and supporting structure having a gap between the porous body and the support is also acceptable as long as the functions of the device according to the present invention are not practically impaired. However, the porous body is preferably fixed and supported in such a manner that the surface portions of the porous body (in the embodiment shown in FIG. 1 and the like, the curved surface of the porous body having a columnar shape laid in the lateral direction) other than the surfaces in contact with the electrodes are brought into contact with the support.

It is desirable that, in the embedded structure, the communicating portion of each rubber electrode is not closed by the support and a space is provided at the communicating portion.

The sandwiched structure 20, including the rubber electrodes, is preferably held and fixed by the support 4. In this embodiment, it is preferable to mold or prepare the support so that the rubber electrodes and the support may be tightly in contact with each other at their contact portions.

The support 4 of the device according to the present invention can be made of resin or rubber material. For example, silicone resin, fluorocarbon resin, polypropylene resin, polyether ether ketone resin, polyimide resin, polycarbonate, polystyrene, polyethylene terephthalate, polypropylene, polymethylpentene, acrylic resin, ABS resin, natural rubber, or synthetic rubber can be used as the material of the support 4. Silicone resin is especially preferable in view of the durability of the compact infusion device, flexibility of the device when attached to the body, moldability in the manufacturing process, adhesiveness with the rubber electrodes 3, the visibility of the inner portions, and the like.

It is preferable that the entire support 4 is made of the material described above. Especially, it is preferable that the parts of the support that are brought into contact with the rubber electrodes 3 are made of the material described above in order to better prevent the leakage of the fluid.

That is, in the present disclosure, it is desirable that at least the parts of the support 4 that are brought into contact with the rubber electrodes 3 are made of resin or rubber material. Furthermore, it is more desirable that the parts of the support 4 that are brought into contact with the rubber electrodes 3 are made of the material described above, preferably silicone resin.

Power Supply Support Portion

In the device according to the present invention, while the porous body of the sandwiched structure 20 is embedded in the support 4, a part of each rubber electrode protrudes outward from the support.

The protruding structures can function as the power supply support portions 32 in the device according to the present invention. That is, in the device according to the present invention, each of the pair of rubber electrodes has a structure protruding outward from the support, and the protruding structures are disposed at positions at which they can directly hold the small batteries.

That is, it is preferable that, in the portions of the pair of rubber electrodes that protrude outward from the support, the structures that can hold the power supply by sandwiching it (the structure for sandwiching and holding the power supply) serve as the power supply support portions 32. More specifically, the power supply support portions are preferably the structures formed by the portions of the pair of rubber electrodes that protrude outward from the support and that can function as the structure for holding the small batteries by sandwiching them (the structure for sandwiching and holding the small batteries). More preferably, the power supply support portions are structures for sandwiching and holding button cells.

It is desirable that the areas of the pair of rubber electrodes constituting the power supply support portions 32 are practically disposed to face each other so that the protruding structures may function as the power supply support portions. In this embodiment, at least parts of the areas that protrude upward from the support or that protrude sideward from the support (in the embodiment shown in FIG. 1 and the like, the sideward direction vertical to the longitudinal direction of the device) are disposed to face each other, and as a result, the protruding structures function as the power supply support portions. In a preferred embodiment, the protruding areas are formed at the upper side of the support.

In these opposing structures, the area functioning as each power supply support portion preferably has a flat surface such that the flat surfaces of respective power supply support portions face each other. When both of the pair of rubber electrodes are flat plate electrodes or the like, it is preferable that the surfaces of respective electrodes are disposed vertical to the longitudinal direction of the device and face each other to form the opposing structure.

Also, when one electrode has an L-shape having a curved structure or the like and the other electrode has a short protruding structure, for example, it is possible to employ a structure in which the electrode surfaces of these electrodes are disposed to face each other in parallel.

It is also preferable that the areas of the rubber electrodes that function as the power supply support portions 32 are molded into shapes suitable for being fitted to the outer edges of the small batteries. The fitting structure can be, but is not limited to, a recessed structure to be fitted to the outer edges of the small batteries or a holder structure to be fitted to the outer sides of the small batteries.

As the small batteries are sandwiched between the surfaces of the pair of electrodes constituting the power supply support portions 32 of the device according to the present invention, the power supply can be fixed and held without using other fixing members or the like. In a preferred embodiment, the small batteries are fitted to the fitting structures of the power supply support portions, and are held by making use of the elasticity of the rubber electrodes.

Here, in order that the fluid is transported downstream in the compact infusion device according to the present invention, the electrode at the fluid supply reservoir side (upstream side) is used as the positive electrode 3a and the electrode at the drug solution holding channel side (downstream side) is used as the negative electrode 3b.

Ordinary small batteries that can be fitted between the electrodes can be used as the small batteries 9, and specifically, button cells are preferable. If desired, members for holding the batteries can be additionally used in some embodiments, though the device according to the present invention does not necessarily require such members. Also, in some other embodiments, members such as an adaptor or a holder can be additionally used to hold the batteries more securely, as long as such members do not cause any problem in view of the weight of the device under usage.

[Fluid Holding Portion]

The component members of the compact infusion device according to the present invention include the fluid holding portion 50. The fluid holding portion 50 is a container-like structure/structures spatially connected to the porous body of the device of the present disclosure and functions to hold a certain amount of fluid inside the device.

That is, preferably, the fluid holding portion 50 according to the present invention is a container-like structure/structures spatially connected to the porous body 2 and is a container-like structure/structures (a container-like structural body/bodies for holding fluid) that function to hold a certain amount of fluid inside the device.

The fluid holding portion 50 according to the present invention is preferably a container-like structure that includes the fluid supply reservoir 51. Moreover, the fluid holding portion 50 according to the present invention is preferably container-like structures that include the fluid supply reservoir 51 and the fluid storage reservoir 53. It is preferable that the fluid holding portion 50 is composed of the fluid supply reservoir 51 only or the fluid supply reservoir 51 and the fluid storage reservoir 53 only.

The term "fluid" as used herein refers to the liquid that is permeated through the porous body of the device of the present disclosure and is used to transmit the fluid driving force to the downstream channel side by the electroosmotic flow phenomenon. It may also be called the driving liquid. Any ordinary liquids that can be used for driving fluid by the electroosmotic pump can be used as the fluid for the device according to the present invention.

The fluid can be water or an alcohol, for example. It is preferable to use ultrapure water having high concentrations of hydrogen and hydroxide ions, methanol, or the like in view of the efficiency of the electroosmotic flow. It is especially desirable to use ultrapure water, preferably sterile ultrapure water, in view of the safety of the device, which is used for infusion purposes.

Fluid Supply Reservoir

The fluid holding portion 50 according to the present invention includes the fluid supply reservoir 51, which is spatially in contact with the communicating portion 31 of one of the rubber electrodes in the sandwiched structure 20 or which is connected to the communicating portion 31 of the one of the rubber electrodes in the sandwiched structure 20 through a member having a space or a channel. That is, the component members of the device according to the present invention include the fluid supply reservoir 51 located upstream from the fluid drive.

The fluid supply reservoir 51 is a container-like structure for holding the fluid that has been introduced into the device and functions to supply the fluid to the porous body. When the device is driven, a suction force toward the direction of the porous body is generated by the fluid driving force inside the porous body, and as a result, the fluid filled in the fluid supply reservoir passes through the upstream rubber electrode 3a and is supplied to the porous body.

The fluid supply reservoir 51 is a container-like structure that is spatially in contact with or connected to the communicating portion of the upstream rubber electrode 3a in the sandwiched structure.

The fluid supply reservoir 51 can be any container-like structure that is spatially in contact with or connected to the communicating portion of the upstream rubber electrode 3a, and for example, the space that is located inside the support and is spatially in contact with the communicating portion of the upstream rubber electrode can be directly used as the fluid supply reservoir. Also, in one possible embodiment, an additional container-like member may be connected to the communicating portion of the upstream rubber electrode, so that the space inside this container-like member is used as the fluid supply reservoir.

In another possible embodiment, a channel or the like may be formed inside the support 4, or a tubular member or the like having a channel may be additionally provided in the support, so that the communicating portion of the upstream rubber electrode and the fluid supply reservoir may be spatially connected through this channel.

In a possible preferred embodiment, a hollow structure is molded inside the support, and a part of the hollow structure is used as the fluid supply reservoir 51.

The fluid supply reservoir 51 can have any size suitable for the compact infusion device, and for example, it can be a space whose volume is approximately 0.01 to 2 mL.

Various shapes can be employed for the fluid supply reservoir 51 as long as the fluid can be held inside. For example, the fluid supply reservoir can be, but is not limited to, a cylindrical space, a polygonal prism space, a circular cone shaped space, a polygonal cone shaped space, a circular truncated cone shaped space, a polygonal truncated cone shaped space, a cube space, a rectangular cuboid space, a spherical space, a space having a shape obtained by the combination of these shapes, or a space having a shape that is substantially equivalent to these shapes.

The fluid supply reservoir 51 preferably has an opening 52 for introducing or discharging the fluid. In a preferred embodiment, the fluid supply reservoir 51 is provided with a lid member 11 for closing the opening 52.

The lid member 11 for closing the opening 52 preferably has a structure for tolerating the negative pressure inside the container that occurs as a result of the generation of the electroosmotic flow.

In an exemplary embodiment, the lid member 11 may be provided with fine ventilation holes so that the pressure balance can be adjusted when negative pressure occurs. Such ventilation holes of the lid member 11 preferably have a shape and size that allow the surface tension of the fluid to be maintained so that the leakage of the fluid can be prevented.

In another exemplary embodiment, the lid member 11 can be made of a covering member of thin soft resin that can be precisely deformed depending on the magnitude of the negative pressure generated inside. For example, the covering member can be a film-like or cling-wrap-like member made of thin soft resin, or a member having functions described above that is used for food-wrapping purposes or the like. In this embodiment, the deformation of the lid member directly serves to adjust the pressure balance when negative pressure occurs, and thus, it becomes unnecessary to provide ventilation holes.

Fluid Storage Reservoir

In some possible embodiments, the fluid holding portion 50 according to the present invention has, in addition to the fluid supply reservoir 51 described above, a fluid storage reservoir 53 which is spatially in contact with the communicating portion 31 of the downstream rubber electrode in the sandwiched structure 20 or which is connected to the communicating portion 31 of the downstream rubber electrode through a member having a space or a channel. That is, in some embodiments, the component members of the device according to the present invention may include the fluid storage reservoir 53 located downstream from the fluid drive.

The fluid storage reservoir 53 can be used as a buffer space for storing the fluid that has been transported from the porous body 2. The fluid storage reservoir 53 is not a necessary structure in embodiments in which the device is used as an ordinary infusion device. Yet, when the fluid drive needs to be driven in the reverse direction, the fluid storage reservoir can then serve as the supply reservoir that can supply the fluid stored therein, and such a device structure is favorable.

The fluid storage reservoir 53 is a container-like structure which is spatially in contact with or is connected to the communicating portion of the downstream rubber electrode 3b in the sandwiched structure 20.

The fluid storage reservoir 53 can have any container-like structure that is spatially in contact with or is connected to the communicating portion of the downstream rubber electrode 3b, and for example, a space that is located inside the support and is in contact with the communicating portion of the downstream rubber electrode can be directly used as the fluid storage reservoir. Also, in another possible embodiment, a separate container-like member may be connected to the communicating portion of the downstream rubber electrode, so that the space inside the container-like member is used as the fluid storage reservoir.

In still another possible embodiment, a channel or the like may be formed inside the support, or a tubular member or the like having a channel may be additionally provided at the support, so that the communicating portion of the downstream rubber electrode and the fluid storage reservoir may be spatially connected through this channel.

In a possible preferred embodiment, a hollow structure is molded inside the support, and part of the hollow structure is used as the fluid storage reservoir 53.

The fluid storage reservoir 53 can have any size suitable for the compact infusion device, and for example, it can be a space whose volume is approximately 0.01 to 2 mL, for example. The shape of the fluid storage reservoir 53 is not particularly limited, and for example, a shape similar to that of the fluid supply reservoir described above can be employed.

The fluid storage reservoir 53 preferably has a hole structure 54 through which the fluid is transported toward the drug solution holding channel. In an exemplary embodiment, a hole structure whose diameter or width is approximately the same as that of the drug solution holding channel 6 can be formed on one of the walls of the fluid storage reservoir.

The hole structure 54 can be formed at any position that allows the downstream transportation of the fluid driven by the fluid driving force from the fluid drive, and in a possible exemplary embodiment, the hole structure may be formed at a part of the downstream-side wall of the fluid storage reservoir. In a preferred exemplary embodiment, the hole structure is provided at the central part of the downstream-side wall of the fluid storage reservoir.

The hole structure 54 can have any shape and size suitable as a fine pore that allows the downstream transportation of the fluid driven by the fluid driving force from the fluid drive, and in a possible exemplary embodiment, the hole structure can have a shape and size approximately equal to that of the cross section of the drug solution holding channel.

[Drug Solution Holding Channel]

The compact infusion device according to the present invention has a channel structure, which is spatially in contact with the communicating portion 31 of the downstream rubber electrode in the sandwiched structure 20 or which is connected to the communicating portion 31 of the downstream rubber electrode through a member having a space or a channel, and which is a member that functions as the drug solution holding channel 6 of the device of the present disclosure. That is, the component members of the device according to the present invention include the drug solution holding channel 6 located downstream from the fluid drive.

The drug solution holding channel 6 is a member that enables to retain a certain amount of drug solution inside the device, and moreover, the drug solution holding channel is a channel structure that transmits the fine fluid pressure generated by the fluid drive 10 to the surface of the drug solution and thereby enables to transport very small amounts of the drug solution inside the channel toward the needle.

Since the drug solution holding channel 6 is a fine channel structure, the fluid and the drug solution are not mixed with each other due to their surface tensions. The fluid driving force of the fluid is transmitted to the surface of the drug solution, and consequently, the downstream movement of the drug solution is driven. Since the fluid driving force is transmitted to the surface of the drug solution without the liquid being mixed with the air because of the surface tension of the liquid inside the fine channel, it is also possible to transmit the fluid driving force by the fine air bubbles generated from the porous body 2.

The term "drug solution" as used herein refers to the solution in general that contains a drug to be administered to humans, animals, or the like. The drug solution as used herein mainly refers to those administered intravenously by infusion or the like. Since the infusion device of the present disclosure can realize the infusion of a very small amount of drug solution, the drug solution used in the present disclosure can be a solution whose drug concentration is remarkably higher than those used for ordinary infusion or for an ordinary infusion device. Moreover, the drug solution in the present disclosure includes those that can be injected subcutaneously.

The drug solution holding channel 6 is a channel structure that is spatially in contact with or connected to the communicating portion 31 of the downstream rubber electrode in the sandwiched structure 20.

The drug solution holding channel 6 can be any channel structure that is spatially in contact with or connected to the communicating portion of the downstream rubber electrode, and for example, a space that is located inside the support and is spatially in contact with the communicating portion of the downstream rubber electrode can be directly used as the drug solution holding channel. In one possible embodiment, an additional tubular member may be connected to the communicating portion of the downstream rubber electrode, so that the space inside the tubular member may be used as the drug solution holding channel.

In another possible embodiment, a space may be formed inside the support or a container-like member having a space may be provided, so that the communicating portion of the downstream rubber electrode and the drug solution holding channel may be spatially connected through this space.

In a possible preferred embodiment, a channel structure is molded inside the support and used as the drug solution holding channel.

The drug solution holding channel 6 preferably has a size that can help generate enough surface tension to prevent the fluid or the air, which has moved from the fluid drive to the drug solution holding channel, from being mixed with the drug solution. Moreover, the drug solution holding channel preferably has a size that allows to transmit the fine pressure from the fluid to the surface of the drug solution. That is, it is preferable that the drug solution holding channel 6 is substantially composed of a fine channel whose maximum channel width is 1 mm or less.

Specifically, it is desirable that the maximum channel width (channel diameter) is 1 mm or less, preferably 0.5 mm or less. The lower limit of the maximum channel width (channel diameter) is 0.02 mm or more, preferably 0.05 mm or more, in order to ensure that a certain amount of the drug solution can be retained inside the channel and to avoid the clogging of the channel.

The wording "substantially composed of" as used herein also includes some cases in which, even if the maximum channel width at some part of the channel may exceed the predetermined value, most part of the channel has the maximum channel width of 1 mm or less, and the entire channel can generate enough surface tension to transmit the driving force to the surface of the drug solution.

The cross section of drug solution holding channel 6 can have any shape that can function as a channel. For example, the cross section can have a circular shape, an oval shape, an elliptic shape, a polygonal shape (a triangular shape, a quadrangular shape, or other polygonal shapes with more sides), a rectangular shape, or a shape that is substantially equivalent to these shapes. A circular shape, a substantially square shape, and the like are especially suitable.

The volume of the entire channel of the drug solution holding channel 6 preferably exceeds a certain level so that a certain amount of drug solution can be held in the device. It is desirable that the volume of the channel portion that can hold the drug solution is 0.01 mL or more, preferably 0.05 mL or more, in order to ensure the amount of liquid suitable for the compact infusion device. The upper limit of the volume can be of any value suitable for the compact infusion device, and for example, when the compact infusion device is used for humans, it is desirable that the volume of the channel portion that can hold the drug solution is 4 mL or less, preferably 2 mL or less.

That is, when the compact infusion device is used for humans, it is desirable that the drug solution of 0.01 to 4 mL can be held in the drug solution holding channel 6. When the infusion device is used for large animals such as horses and cattle, it is possible to employ a drug solution holding channel 6 whose capacity is approximately 10 mL, though the weight of the device may become larger.

The term "channel portion that can hold the drug solution" indicates the part of the drug solution holding channel in which drug solution can be practically stored. In an exemplary embodiment, it can be the space inside the entire channel that extends from the one-way valve 61 to the needle holding portion 7 (needle holding structure).

With regard to the entire channel shape of the drug solution holding channel 6, it is desirable that the drug solution holding channel includes curved tubular portions in order to hold a certain amount of drug solution inside the limited space of the device. It is desirable that the drug solution holding channel includes 2 or more curved tubular portions, preferably 3 or more curved tubular portions, more preferably 4 or more curved tubular portions, and even more preferably 6 or more curved tubular portions. A channel 62 having a complex structure that includes a plurality of curved tubular portions is suitable for the entire shape of the drug solution holding channel. For example, the entire shape of the channel can be, but is not limited to, an S shape, a continuous S shape, a serpentine shape, a helix shape, or a shape obtained by the combination of these shapes.

The drug solution holding channel 6 preferably has the one-way valve 61. The one-way valve 61 is a valve member that prevents the reverse flow of the liquid from downstream to upstream, while it allows the flow from upstream to downstream.

The one-way valve 61 can be disposed at any position in the main channel of the drug solution holding channel, and it is preferably disposed at an upstream position of the main channel of the drug solution holding channel. In an exemplary preferred embodiment, when a drug solution introducing channel 64 is provided as a branch of the drug solution holding channel, the one-way valve is disposed at a position more upstream than the drug solution introducing channel in order to prevent the drug solution from flowing toward the fluid drive.

In addition to the main channel through which the drug solution is transported, the drug solution holding channel 6 can have branched channels that are used for various purposes.

In a possible exemplary embodiment, liquid-passing channels branched from the main channel can be provided. For example, two or more liquid-passing channels are provided, and the drug solution can be filled into the device through one liquid-passing channel and discharged through another liquid-passing channel in order to adjust the pressure and dispose of residual drug solution. That is, in this embodiment, liquid-passing channels that can be used as the drug solution introducing channel 64 and/or the drug solution discharge channel 65 are provided. In a possible exemplary embodiment, the upstream liquid-passing channel can be used as the drug solution introducing channel and the downstream liquid-passing channel can be used as the drug solution discharge channel.

The end of the liquid-passing channel preferably has a fine opening that opens to the outside of the device. In an exemplary embodiment, when the drug solution holding channel 6 is a channel molded inside the support 4, the liquid-passing channel branches toward and opens to the outside of the support. In this embodiment, the liquid-passing channel can branch from the main channel in the vertical or horizontal direction and the opening of the liquid-passing channel can be formed at the upper or side surface of the support.

In another embodiment, when the drug solution holding channel 6 is made of a tubular member, the opening of the tube branched from the main channel can be located outside the device.

It is preferable that a stopper member 12 capable of sealing the channel can be attached to the opening of the branched channel so that the opening can be opened and closed as desired. For example, it is desirable that the opening of the drug solution introducing channel 64 and the opening of the drug solution discharge channel 65 are opened when the drug solution is filled into the device, and these openings are closed when the compact infusion device is used.

Any members that can seal the opening of the channel can be used as the stopper member 12, and ordinary stopper members having a simple structure, such as a cap, a stopper, a plug, or a seal, can be used.

Moreover, in some possible embodiments, in addition to the branched channel structures that serve as the liquid-passing channels, other branched channel structures through which members can be installed into the main channel can also be provided. It is preferable that the opening of such branched channel structures can also be closed when the compact infusion device is used.

[Needle Holding Portion (Needle Holding Structure)]

It is preferable that the injection needle 8 can be directly or indirectly connected to a part of the channel structure of the drug solution holding channel 6. That is, it is preferable that a hollow structure at which the channel and the needle are directly or indirectly connected can be formed at a part of the drug solution holding channel 6.

Any part of the main channel of the drug solution holding channel can be selected as the connecting position of the injection needle 8, and it is desirable that the connecting position is located at a downstream region of the main channel, preferably the downstream end of the main channel or the vicinity thereof. The connecting position is preferably located at the end of the main channel so that a certain amount of the drug solution can be stored.

The injection needle 8 is preferably connected by a channel structure that can function as the needle holding portion 7 or by a separate holding member.

The needle holding portion 7 is a structure that can be connected to and hold the needle 8 (a structure for being connected to and holding the needle).

In an exemplary embodiment, a part of the main channel is molded as a structure that functions as the needle holding portion 7, and the main channel and the injection needle can be connected directly. In this embodiment, the base portion of the injection needle is directly fitted to the main channel, and the inner portions of the hollow structures of the main channel and the needle are spatially connected to each other.

In another embodiment, a separate holding member 7 for fixing and holding the needle can be provided, so that the needle can be connected indirectly. In this embodiment, the hollow member 7 for holding the injection needle can be provided at the main channel, for example, and the inner portions of the hollow structures of the main channel and the needle are spatially connected to each other through this hollow member.

Any hollow tubular member through which liquid can pass and which can mediate that connection between the drug solution holding channel 6 and the injection needle 8 can be used as the hollow member 7 for holding the needle. For example, just like the support described above, soft resin or hard resin can be employed for the hollow tubular member.

The injection needle 8 can be connected at any angle that allows the tip of the needle to be directed to a position suitable for the usage as the compact infusion device. For example, the needle can be designed to be connected at any angle that allows the tip of the needle to be directed downward from the horizontal direction of the compact infusion device.

The angle at this connecting position can be set as desired by adjusting the angle of the end region of the main channel of the drug solution holding channel 6. It is also possible to employ a curved tubular structure as the hollow member 7 for holding the needle to adjust the angle at the connecting position as desired.

Any injection needle suitable for the compact infusion device can be used as the injection needle 8 of the device of the present disclosure, and it is desirable to use an injection needle having a long, fine shape suitable for infusing a very small amount of drug solution or the like at high accuracy. It is also preferable that the injection needle 8 can be used even if the needle is deformed to some extent when it is inserted into the blood vessel or when the device is attached to the body and some pressure is applied to the needle.

In an exemplary embodiment, the injection needle 8 can be a fine hollow structure having an outer diameter of 80 to 600 μm, preferably about 100 to 300 μm. The needle length can be 5 to 200 mm, preferably about 10 to 150 mm, for example. The material of the needle can be, but is not limited to, stainless steel, titanium, or resin, for example. If desired, coating or the like can be applied to the inner wall of the needle 8 in order to prevent clogging. A needle which is minimally invasive at the time of insertion or attachment to the body is especially preferable.

A cannula needle, a catheter needle, or the like can also be used as the injection needle 8 depending on the purpose of use of the infusion device.

[Entire Structure of the Device]

The device 1 of the present disclosure may include the component members described in the paragraphs above. In an exemplary embodiment, it is preferable that the entire support 4 is molded as an integrated structure including the component members of the device, in view of the prevention of leakage, the simplification of the manufacturing process, the enhancement of the strength of the device, and the like. More specifically, it is desirable that, among the two or more members constituting the support 4, one member, or two or more members, are molded in advance, and the support is structured by the combination of these members. It is especially preferable that the spaces and the channel structures constituting the drug solution holding channel 6, the fluid holding portion 50, and the like are constructed in this manner.

In a preferred embodiment, the device of the present disclosure has lid members that can be attached to the openings.

In one possible embodiment of the device 1, some of the component members described in the paragraphs above may be provided in plurality if desired. In an exemplary embodiment, two or more fluid drives 10 may be provided. In another exemplary embodiment, two or more injection needles 8 may be provided. In still another exemplary embodiment, the drug solution holding channel 6 may be provided with two or more main channels, so that two or more different kinds of drug solutions can be administered.

The device 1 of the present disclosure may be provided as a device before the porous body 2 is immersed in the fluid. It may also be provided after the porous body 2 is immersed in the fluid. Moreover, the device may be provided before the fluid is contained in the fluid holding portion 50. The device may also be provided after the fluid is contained in the fluid holding portion 50.

In other words, the compact infusion device according to the present invention includes the product whose porous body is not immersed in the fluid. Moreover, the compact infusion device according to the present invention includes the product whose fluid holding portion does not contain the fluid.

Further, the compact infusion device according to the present invention includes the product whose porous body is immersed in the fluid. Also, the compact infusion device according to the present invention includes the product whose fluid holding portion contains the fluid.

The compact infusion device according to the present invention also includes the product whose porous body is immersed in the fluid and whose fluid holding portion contains the fluid.

The device 1 of the present disclosure may be provided as a device before the drug solution is contained in the drug solution holding channel 6. It may also be provided after the drug solution is contained in the drug solution holding channel 6.

That is, the compact infusion device according to the present invention includes the product whose drug solution holding channel 6 does not contain the drug solution. The compact infusion device according to the present invention also includes the product whose drug solution holding channel 6 contains the drug solution.

The device 1 of the present disclosure may be provided as a device after the injection needle 8 is connected to the device. The device may also be provided before the injection needle 8 is connected to the device.

That is, the compact infusion device according to the present invention includes the product to which the injection needle is not connected. The compact infusion device according to the present invention also includes the product to which the injection needle is connected or which is provided with the injection needle connectable to the device.

The device 1 of the present disclosure may be designed to include various component members or various means as well as the members described above, as long as they do not substantially affect the portability and the like of the device.

In an exemplary embodiment, the device may be provided with various sensors, wireless transmission means, or the like. If desired, the device may be provided with a holder, an adapter, a cover, a case, or the like in order to protect the sandwiched batteries during usage. A cover, a case, or the like for protecting the entire device can also be employed. If desired, a switching means which can perform an ON/OFF switching operation of the power supply can be employed.

In another exemplary embodiment, the device 1 can be designed to have enhanced portability by being provided with members such as a holding member or an engagement member that help the device to be attached to the human body or the like.

When the device 1 of the present disclosure is provided as a product, its component members may be already connected to the device so that the device may be ready for operation, but in one embodiment, the component members may be provided being connectable to the device. In another embodiment, the device may be provided as a system including these component members.

That is, when the device according to the present invention is provided as a product, it can be provided as a portable compact infusion device system that includes the component members of the device described above. It can also be provided as an assembly kit for the portable compact infusion device that includes the component members of the device described above.

The wording "the component members being connectable to the device" as used herein also includes the embodiments in which the component members are physically separated from the main body of the device but can be easily connected thereto.

2. Operating Modes, Specifications, and the Like of the Device Described Above

The operating modes, the specifications, and the like of the compact infusion device 1 according to the present invention will be described in this section.

[Operating Modes]

If the device of the present disclosure does not contain the fluid when it is manufactured, the fluid is filled into the device prior to the usage of the device, and then the device is put into use.

The operation for filling the fluid into the device is preferably executed through the opening 52 of the fluid supply reservoir. With this operation, the porous body 2 can be immersed in the fluid, and the fluid holding portion 50 can contain the fluid. It is also possible that the porous body 2 is immersed in the fluid in advance when the component members are assembled during the manufacturing process of the device.

It is desirable to close the opening with the lid member 11 after the fluid is filled into the device.

The device of the present disclosure is used after the drug solution is filled into the drug solution holding channel at a stage before usage. The operation for filling the drug solution into the device is preferably executed through the opening of the drug solution introducing channel 64. With this operation, the drug solution can be filled into the drug solution holding channel 6. It is desirable to close the opening with the stopper member 12 after the drug solution is filled into the device.

In the device of the present disclosure, the operation for driving the fluid can be initiated by inserting the small batteries 9 between the power supply support portions 32. When the device is additionally provided with a power control means, the drive operation can be initiated by operating the switch.

In the device of the present disclosure, the small batteries are inserted such that the positive side is connected to the upstream electrode 3a and the negative side is connected to the downstream electrode 3b. Consequently, electroosmotic flow that moves the fluid inside the porous body 2 downstream can be generated, the fluid driving force is transmitted to the drug solution, and the device can function as a compact infusion device.

That is, when the fluid drive of the device of the present disclosure is driven, the fluid drive generates the driving force that transports the fluid at a position nearer the fluid supply reservoir than the pair of rubber electrodes toward a position nearer the drug solution holding channel than the pair of rubber electrodes, and the driving force is transmitted downstream to transport the drug solution held inside the drug solution holding channel toward the injection needle.

[Specifications]

Since the device of the present disclosure utilizes the principle of electroosmotic flow as a means for generating the fluid driving force, liquids can be transported with high precision at an amount incomparably smaller than those transported by an ordinary motor-driven pump or the like. The infusion flow rate performed by the device of the present disclosure can be adjusted by changing various factors such as the material of the porous body, the material of the electrodes, the arrangement of the sandwiched structure, and the power source type. Depending on the embodiment, the flow rate can be adjusted within a range of 1 to 10,000 nL/min, preferably 1 to 5,000 nL/min, and more preferably 1 to 1,000 nL/min.

The lower limit of the flow rate that can be controlled by the device of the present disclosure is as low as 1 to 100 nL/min, preferably 1 to 50 nL/min, more preferably 1 to 20 nL/min, and even more preferably 1 to 10 nL/min, for example. That is, the device of the present disclosure makes it possible to perform infusion from the injection needle without pulsation at flow rates of 100 nL/min or less, preferably 50 nL/min or less.

Moreover, since the device of the present disclosure can realize infusion at precise, very low flow rates, it becomes possible to use a highly concentrated drug solution, and a drug solution holding channel whose capacity is minimized down to several ten microliters to several milliliters can be used as the drug solution reservoir.

Further, since the device of the present disclosure can realize infusion at precise, very low flow rates, it becomes possible to continuously administer a drug solution for long hours directly to the exact diseased part of the body by subcutaneous injection.

Also, since the device of the present disclosure utilizes the principle of electroosmotic flow to generate the fluid driving force, this device does not theoretically cause pulsations.

The device of the present disclosure has a simple structure in which the fluid drive 10 is formed by the combination of the porous body 2 and the rubber electrodes 3. The device can achieve excellent durability and can be used continuously for several hours to several ten hours.

Since a fine channel structure is employed as the drug solution holding channel 6 of the device of the present disclosure, even if fine bubbles are produced during the generation of electroosmotic flow, the fine bubbles do not get mixed in with the drug solution because of the surface tension of the liquid inside the fine channel. Therefore, even if fine bubbles are generated in the porous body 2 of the device of the present disclosure, the movement of the fine bubbles toward the drug solution is prevented.

Since the operations as described above can be achieved just by using low-voltage power source, a compact infusion device excellent in power saving can be provided. In order to ensure the movement of the device of the present disclosure, it is desirable to use small batteries 9 that can generate a voltage of 0.5 to 30 V, preferably 1.5 to 18 V and more preferably 1.5 to 9 V. It is desirable to use button cells in order to save the weight of the device. In preferred embodiments, one to six button cells are connected in series.

In the device of the present disclosure, the sandwiched structure 20 in which the porous body is held by the rubber electrodes makes it possible to form the power supply support portions 32 that are formed by the protruding structures of the pair of rubber electrodes. As a result, small batteries can be held and maintained without using any additional members.

Moreover, in the device of the present disclosure, the contact between the support 4 and the protruding portions of the rubber electrodes makes it possible to prevent leakage of fluid without using any additional members.

Since the entire structure of the device 1 of the present disclosure is remarkably simple and compact, a compact infusion device excellent in portability whose weight is 20 g or less can also be provided. Specifically, it becomes possible to provide a compact infusion device whose total weight including the fluid drive 10, the fluid holding portion 50, the drug solution holding channel 6, and the support 4 is 20 g or less, preferably 10 g or less.

Also, with the device 1 of the present disclosure, it becomes even possible to provide a compact infusion device whose total weight including the needle holding portion 7 and/or the injection needle 8 as well as the members described above is below the aforementioned values.

In addition, with the device 1 of the present disclosure, it becomes even possible to provide a compact infusion device whose total weight including the lid member 11 and/or the stopper member 12 as well as the members described above is below the aforementioned values.

Moreover, with the device 1 of the present disclosure, it becomes even possible to provide a compact infusion device whose total weight including the fluid and/or the drug solution as well as the members described above is below the aforementioned values.

Furthermore, with the device 1 of the present disclosure, it becomes even possible to provide a compact infusion device whose total weight including the small batteries 9 as well as the members described above is below the aforementioned values.

In an embodiment where weight saving is a priority, the device 1 of the present disclosure preferably does not include additional members other than the main structures described above. In an exemplary embodiment, the compact infusion device may be composed of the fluid drive 10, the fluid holding portion 50, the drug solution holding channel 6, and the support 4.

In one possible embodiment, the device 1 of the present disclosure can be formed by the combination of members essential for usage, with no additional members included, such that weight saving can be realized. In an exemplary embodiment, the members of the compact infusion device may consist of the fluid drive 10, the fluid holding portion 50, the drug solution holding channel 6, the support 4, and the needle holding portion 7. In another exemplary embodiment, the members of the compact infusion device may consist of the fluid drive 10, the fluid holding portion 50, the drug solution holding channel 6, the support 4, the needle holding portion 7, and the injection needle 8.

In still another exemplary embodiment, the lid member 11 (preferably, the covering member 11) may be attached to the compact infusion device that consists of the members described above. In yet another exemplary embodiment, the stopper member 12 may be attached to the compact infusion device that consists of the members described above.

In still yet another exemplary embodiment, a compact infusion device containing the fluid can be provided. In a further exemplary embodiment, a compact infusion device containing the drug solution can be provided. In another further exemplary embodiment, a compact infusion device to which the small batteries 9 are attached can be provided.

The device of the present disclosure can have a structure in which the electrode and the power supply support portion are formed integrally, being made of rubber material only, thereby realizing a device structure which can be easily disassembled upon disposal. In one embodiment, when rubber electrodes containing carbon are employed as the rubber electrodes 3, it becomes possible to manufacture the main body of the device without using any metal members, and the disposability of the device can be remarkably enhanced.

Moreover, since the device of the present disclosure has a very simple structure with few component members, the production process of the device can be simplified. Also, the component members of the device can be manufactured at a low material cost.

Because of the component members and the production processes of the device of the present disclosure, this device can be composed only of members which can be manufactured easily and have easy disposability, and consequently, can be suitably provided as a disposable device. There are also many advantages in terms of manufacturing costs.

As described above, the device 1 of the present disclosure can be manufactured as a compact infusion device that is easily portable and inexpensive, and that can be used safely.

Moreover, since the device of the present disclosure can realize micro-drip intravenous administration for long hours, micro-drip intravenous injection for long hours, and micro-drip subcutaneous injection for long hours, and moreover, has a size and a weight suitable for carrying, this device is expected to be used as a technique alternative to intravenous drip in the medical field and the like.

EXAMPLES

Hereinafter, the present invention will be explained by way of examples, but the scope of the invention is not limited thereto. The device produced in these examples will be described below with reference to the structural diagrams and the like.

[Example 1] Production of Compact Infusion Device

A compact infusion device 1 having the components as described below was produced as one embodiment of the compact infusion device according to the present invention.

The device 1 in this example is a compact infusion device whose main components are the fluid drive 10, the fluid holding portion 50, the drug solution holding channel 6, and the needle holding portion 7 as described below.

(1) Fluid Drive

The fluid drive 10 of this device is a structural body in which the porous body 2 is sandwiched by the pair of rubber electrodes 3 containing carbon. In this device, the sandwiched structure 20 in which the porous body 2 is sandwiched by these electrodes serves as the electroosmotic flow pump that supplies fluid driving force to the drug solution holding channel 6.

The porous body 2 is a cylindrical member made of porous ceramic material, and in this device, the cylinder is placed lengthwise, such that its two side surfaces 21 are circular surfaces. With regard to the size of the porous body 2, the diameter of the circular flat side surface is 4 mm, and the length between the two side surfaces is 6 mm. The porous ceramic material of the porous body 2 has an average pore size of 0.5 μm.

Each rubber electrode 3 of this device is a substantially rectangular plate member having a communicating hole 31 provided at the central lower part of the rubber electrode. It is a rubber electrode containing carbon (manufactured by Tigers Polymer Corporation) having a volume specific resistivity of 100 Ω·cm or less. The rubber electrode has a height of 15 mm, a width of 8 mm, and a thickness of 3 mm.

The communicating hole 31 of the rubber electrode is a hole structure formed such that the two sides of the plate member communicate with each other. The cross section of the through hole has a circular shape with an inner diameter of 3.8 mm, and the through hole is formed such that the center of the circle is located at a position 4 mm from the lower end of the rubber plate electrode.

A structure depressed into a shallow disk shape is formed at the upper part of each rubber plate electrode. This is the structure 32 for holding the small batteries, which is a structure to be fitted to the button cells. On the upstream rubber plate electrode 3*a* located at the fluid supply reservoir side, this structure 32 is molded so as to fit to the plus pole of the battery. On the downstream rubber plate electrode 3*b* located at the fluid storage reservoir side, this structure 32 is molded so as to fit to the minus pole of the battery. The lower edges of these structures 32 are disposed such that, when the rubber electrodes are fitted to the support 4, the button cells are brought into contact with the upper surface of the support.

In this device, the plate surfaces of respective rubber electrodes are disposed to face respective circular flat side surfaces 21 located at the two ends of the porous body 2 to form a structure 20 in which the porous body is sandwiched by the pair of rubber electrode plates. When viewed from the side, the center of the communicating hole 31 of each electrode is disposed to coincide with the center of each circular flat side surface of the porous body. Since the diameter of the communicating hole of the electrode is designed to be smaller than the diameter of the circular flat side surface of the porous body, the circumference of the communicating hole of respective rubber electrodes can be tightly fixed to respective circular flat side surfaces of the porous body, such that the porous body can be sandwiched. In the sandwiched structure of this device, the liquid at the communicating hole of one rubber electrode cannot structurally move to the communicating hole of the other rubber electrode unless it passes through the porous body.

In this device, the aforementioned members of the fluid drive 10 are fixed and held by the support 4 that has a rectangular plate shape.

The support 4 in this example is a soft resin member made of polydimethylsiloxane (PDMS), which is a silicone resin, and has a substantially rectangular shape with a length of 53 mm, a width of 15 mm, and a height of 8 mm. The support 4, except for the channels, is molded by directly solidifying the PDMS resin. The hollow or tubular structures described below are molded on two plate members in advance, the two plates are fitted to each other, and thereby the support 4 is formed. The two plate members (the upper plate member and the lower plate member) are stuck to each other, heated, and molded, and the support of this device is obtained.

Thanks to the characteristics of PDMS, the support 4 of this device has enough strength to hold the component members of the device and can be brought into tight contact with the rubber plate electrodes at the contact portions between the support and the rubber electrodes. Moreover, since PDMS is a material with high transparency, the drug solution or the like inside the drug solution holding channel can be observed from outside the device. The support also has excellent flexibility when attached to the body.

When the support 4 of this device is placed such that one of the flat plate surfaces faces downward, the tubular hollow structure 5 is formed so as to extend in a lateral direction (the longitudinal direction of the support) from the side surface at the left short side to a position 20 mm from the left short side. The cross section of this tubular hollow structure has a circular shape with an inner diameter of 4 mm, and the center of the circle coincides with the center of the plate-shaped support when viewed from the left short side. The opening 52 on the side surface of the hollow structure can be used as the liquid-passing opening for introducing or discharging the fluid.

The tubular structure has a shape suitable for tightly fixing the porous body 2 when the porous body having circular flat surfaces and laying lengthwise is inserted horizontally in the longitudinal direction.

As structures that join the tubular hollow structure 5 of the support 4, two rectangular communicating structures that vertically extend from the top surface to the bottom surface of the support are formed in parallel with each other. The rectangular communicating structure is a through-hole structure in which, when viewed from the top of the support, the height of the rectangle (the length in the short side direction of the support) is 8 mm and the width of the rectangle (the length in the long side direction of the support) is 3 mm. The through-hole structure is a through hole having a shape suitable for tightly inserting the rubber electrode 3 into the support, with the short side of the rubber electrode directed downward and the plate surface facing the short side surface of the support.

The rectangular communicating structure is formed such that, when viewed from the top of the support 4, the center of each rectangular communicating structure coincides with the center line of the tubular hollow structure 5. As the rectangular communicating structures are disposed this way, each rectangular communicating structure makes right angles with the tubular hollow structure. The two rectangular communicating structures are disposed in parallel with each other, placed 6 mm apart from each other.

In this device, the porous body 2 is disposed between the two rectangular communicating structures in the tubular hollow structure 5, and the rubber plate electrodes 3 are inserted into respective rectangular communicating structures, thereby forming the structure 20 in which the porous body is brought into contact with and sandwiched between the two rubber plate electrodes. This structure functions as the fluid drive 10 and can be obtained by a very simple operation, just by inserting necessary members into the device. Since both the rectangular communicating structure and the rubber plate electrode have elasticity, they are brought into tight contact with each other at their contact portion and the liquid inside does not leak through the contact portion.

In this device, the upper portions of the two rubber plate electrodes that protrude from the support 4 can directly serve as the power supply support portions 32 without using any other additional members. In this device, button cells 9 can be fixed and held only by fitting the button cells between the two rubber plate electrodes, because the two rubber plates have holding force and have concaved structures that serve as the power supply support portions.

(2) Fluid Holding Portion

In the tubular hollow structure 5 of this device, the space located upstream of the fluid drive 10 functions as the reservoir for supplying fluid to the fluid drive. That is, this space serves as the fluid supply reservoir 51, which is the upstream fluid holding portion. The fluid supply reservoir 51 is a cylindrical space with a diameter of 4 mm and a length of 4.7 mm. The opening at the left side of this space can be provided with a lid structure. This opening 52 at the side surface of the fluid supply reservoir 51 can be used as the liquid-passing port for introducing or discharging the fluid. The opening can be provided with the covering member 11 made of thin soft resin, which serves as a lid member that can be attached and peeled off as desired. In this device, polyethylene film was used as the covering member.

Further, in the tubular hollow structure 5 of this device, the space located between the drug solution holding channel 6 and the fluid drive 10 functions as the buffer space for storing the fluid that has been transported from the fluid drive. That is, this space serves as the fluid storage reservoir 53, which is the downstream fluid holding portion. The fluid storage reservoir 53 is a cylindrical space with a diameter of 4 mm and a length of 2.6 mm. A wall, which is the end of this hollow structure, exists on the downstream side of this space, but the hole structure 54 that communicates with the drug solution holding channel 6 is provided on the central portion of this wall.

(3) Drug Solution Holding Channel

In the support 4 of this device, the drug solution holding channel 6 is provided further downstream of the space forming the fluid storage reservoir 53. The drug solution holding channel 6 is a tubular structure whose function is to store and hold the drug solution and transport a very small amount of the drug solution toward the injection needle by the pushing force of the fluid that has been transported from the fluid drive.

The drug solution holding channel 6 is a fine tubular channel structure formed inside the support and is a tubular structural body whose cross section has a substantially square shape with a side length of 0.5 mm. In this device, a groove is molded into the lower plate member of the support in advance, while the portion of the upper plate member that fits to the groove is provided as a flat surface. The two plate members are fitted to each other, and thereby the channel structure is formed.

The main channel of the drug solution holding channel 6 is disposed horizontally to be located at the vertical center of the support 4 when viewed from the long side surface of the support. The upstream side of the main channel of the drug solution holding channel 6 communicates with the side wall located at the most downstream side of the fluid storage reservoir 53. When viewed from the top of the support, this communicating portion 54 is provided at the central portion with respect to the shorter width of the support.

In the main channel of the drug solution holding channel 6, a straight tube of approximately 10 mm extends downstream from the communicating portion 54. In this straight tube, a one-way valve 61 is provided at a position about 5 mm from the communicating portion 54 communicating with the fluid storage reservoir. The one-way valve 61 is a valve member that allows the liquid to flow from upstream to downstream but prevents the liquid from flowing from downstream to upstream.

A channel having an S-shaped serpentine structure having continuous curves is formed downstream of the one-way valve. In this example, the S-shaped serpentine channel 62 that has 2.5 cycles of S-shaped curves is provided as shown in FIG. 1. Each curve forms a right angle and has an inner corner radius (R) of 0.5.

A straight tube that communicates with the hollow structure of the needle holding portion 7 is provided downstream of the S-shaped curved structure.

In the drug solution holding channel 6, the drug solution can be filled into and held inside the space that is located between the one-way valve and the needle holding portion 7 and that has a capacity of 50 μL.

In this device, the drug solution holding channel 6 has upward channel structures, which form liquid-passing channels branched from the drug solution holding channel and communicating with the upper surface of the support 4. Each liquid-passing channel is a tubular channel whose cross section is circular and has an inner diameter of 1 mm, and a part of the support 4 directly serves as the wall of the channel.

In this device, liquid-passing channels are provided at two positions in total: one liquid-passing channel is provided at the starting point of the S-shaped curved structure, and the other liquid-passing channel is provided at the ending point of the S-shaped curved structure. In this device, these liquid-passing channels are tubular structures that vertically connect the upper surface of the support 4 and the drug solution holding channel 6, and function as channels that allow the liquid to be supplied from or discharged to the outside of the device. In this example, the upstream liquid-passing channel serves as the drug solution introducing channel 64 and the downstream liquid-passing channel serves as the drug solution discharge channel 65.

The opening of each liquid-passing channel that opens to the upper surface of the support is provided with a structure that can be fitted to the stopper member 12, and the drug solution holding channel 6 can be sealed by attaching the stopper member 12 to the opening.

The schematic drawing in FIG. 2 indicates that this device has another similar channel structure 63 provided in the upstream vicinity of the one-way valve, but this is a structure provided to install the one-way valve 61, and its opening portion on the upper surface of the support is closed by heating PDMS during the last steps of the production process.

(4) Needle Holding Portion (Needle Holding Structure)

The device in this example has a needle holding tube 7 which is connected to and holds an extra-fine injection needle and which is provided in the support 4 at the side opposite to the opening 52 of the fluid supply reservoir.

In this device, the needle holding tube 7 is a tubular hollow member that is made of polyether ether ketone and that has an inner diameter of 0.17 mm and a length of 30 mm. One end of the needle holding tube 7 is disposed such that its hollow tubular structure is connected to the most downstream side of the drug solution holding channel 6, and part of this tubular member is embedded and fixed in the support at a position that extends 3 mm from the side surface of the support.

The injection needle 8, which is used for insertion when drug solution is injected, has its base portion fixed to the inside of the needle holding tube 7, and the tip portion of the injection needle 8 protrudes toward the downstream side. The injection needle 8 in this device is a lancet-type hollow needle which is made of stainless steel having a length of 40 mm, whose outer diameter of the hollow structure is 150 μm, and which has a long, extra-fine needle shape. The hollow structure of the needle has a straight tubular shape but has appropriate elasticity, so the needle can be deformed to some extent when it is inserted into the blood vessel or the like, or when the device is attached to the body and some pressure is applied to the needle. Since an extra-fine long needle is employed in this device, it is minimally invasive at the time of insertion or attachment to the body.

(5) Process for Filling Fluid

After the components of the device were assembled, the openings of the liquid-passing channels for the drug solution and the fluid were opened. The fluid was filled into the fluid supply reservoir 51 through the opening 52 of the fluid supply reservoir, and the device was left to stand until the fluid permeated through the porous body 2. Then, the fluid was further filled into the fluid supply reservoir 51, and a covering member 11 made of thin soft resin was attached and stuck to the opening 52 so that the covering member would be in tight contact with the surface of the fluid filled into the opening. In this device, sterile ultra-pure water was used as the fluid (driving liquid).

In this state, two CR1616 button cells (6 volts) manufactured by Hitachi Maxell Ltd. were inserted in series between the pair of rubber plate electrodes 3 so that they would be fitted to the power supply support portions 32 of the rubber electrodes, and the electroosmotic flow pump was driven. The button cells 9 were disposed such that the positive side was connected to the upstream rubber plate electrode 3*a* and the negative side was connected to the downstream rubber plate electrode 3*b*. When the fluid reached the one-way valve 61 by the driving force generated, the button cells 9 were removed to stop driving, the stopper member 12 was attached to the opening of each liquid-passing channel, and openings were closed. Then, the covering member 11 was removed to inject more fluid into the fluid supply reservoir 51, and the covering member 11 was attached and stuck again to the opening so that the covering member would be in tight contact with the surface of the fluid filled into the opening.

[Example 2] Movement and Specifications of the Device

The movement and the like of the compact infusion device produced in the example above were examined.

In the compact infusion device produced in Example 1, the stopper members were removed from the openings of the drug solution introducing channel and the drug solution discharge channel, and a liquid sample was introduced into the drug solution holding channel through the opening of the drug solution introducing channel. When the liquid sample was filled until it overflowed from the opening of the drug solution discharge channel, the stopper members were attached to the two openings, and the openings were closed. Then, two CR1616 button cells (6 volts) manufactured by Hitachi Maxell Ltd. were inserted in series between the pair of rubber plate electrodes such that they fitted to the power supply support portions of the rubber electrodes, and the electroosmotic flow pump, which served as the fluid drive, was driven.

It was confirmed that, in the compact infusion device produced in the example above, the liquid sample held in the drug solution holding channel could be delivered at very low flow rates to the tip of the extra fine long needle just by fitting the button cells between the pair of rubber plate electrodes. Moreover, very small amounts of liquid could be stably transported without any pulsation, and no leakage of liquid was observed.

Figure 5A:
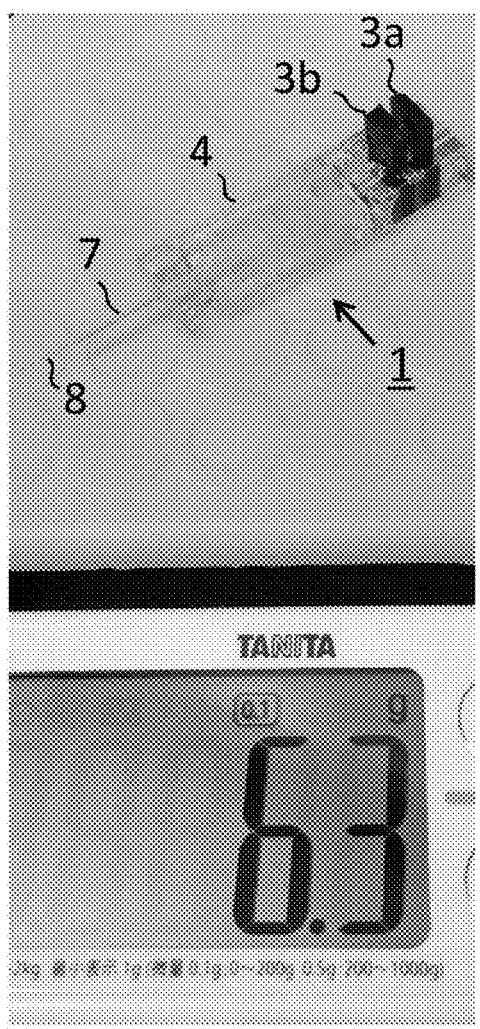
FIGS. 5A and 5B are the photographic images showing the weight of the compact infusion device of Examples 1 and 2.
Figure 5B:
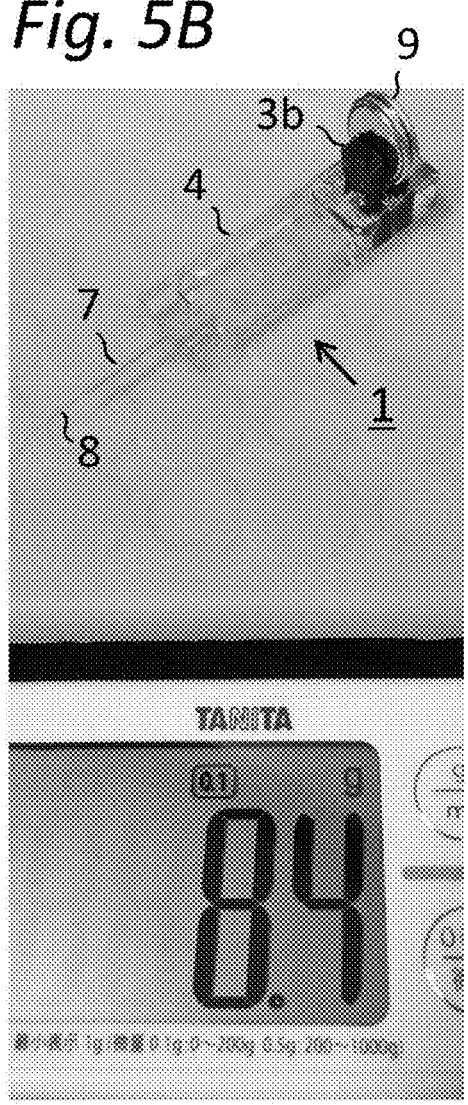

Further, the device of the example above was proved to be an extremely light compact infusion device: the weight of the device containing the fluid and the liquid sample (which corresponds to the drug solution) was only 6.3 g, and even when the button cells were inserted, the total weight of the device was only 8.4 g. FIGS. 5A and 5B are the photographic images of the device.

[Example 3] Processing Example of the Device

Another compact infusion device different from the one produced in the example above was produced and subjected to trimming, and the movement and the like of this compact infusion device were examined.

A compact infusion device was produced following the procedures of Example 1, and the support was subjected to trimming. Here, the portions of the support unnecessary for the device were removed to reduce the weight of the device.

Then, the liquid sample was filled into the drug solution holding channel following the procedures of Example 2, three CR1616 button cells (9 volts) manufactured by Hitachi Maxell Ltd. were inserted in series between the pair of rubber electrodes such that they fitted to the power supply support portions of the rubber electrodes, and electroosmotic flow pump, which served as the fluid drive, was driven.

It was confirmed that, in the compact infusion device produced in this example, very small amounts of the liquid sample filled in the drug solution holding channel could be delivered to the tip of the extra fine long needle just by fitting the button cells between the pair of rubber plate electrodes. Moreover, very small amounts of liquid could be stably transported without any pulsation, and no leakage of liquid was observed.

Figure 6A:
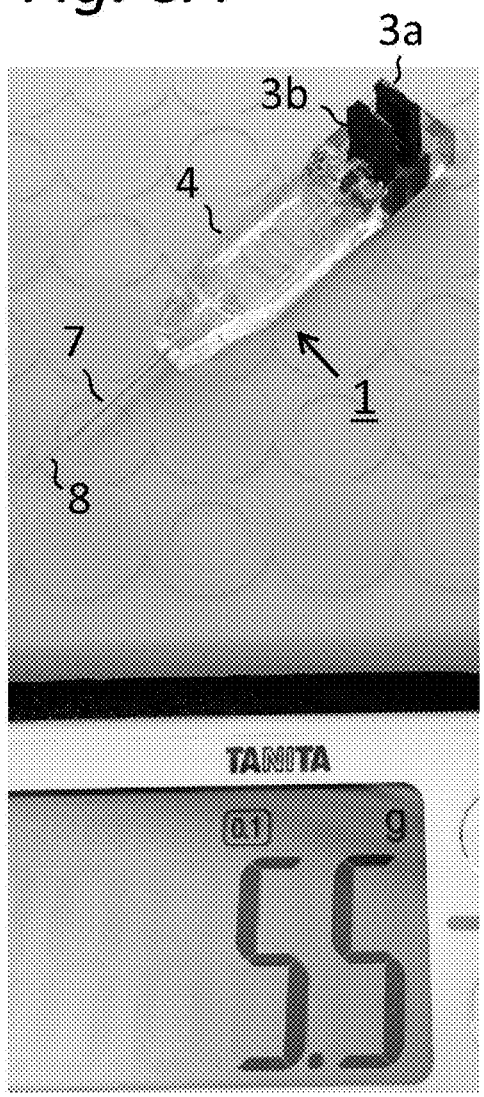
FIGS. 6A and 6B are the photographic images showing the weight of the compact infusion device of Example 3.
Figure 6B:
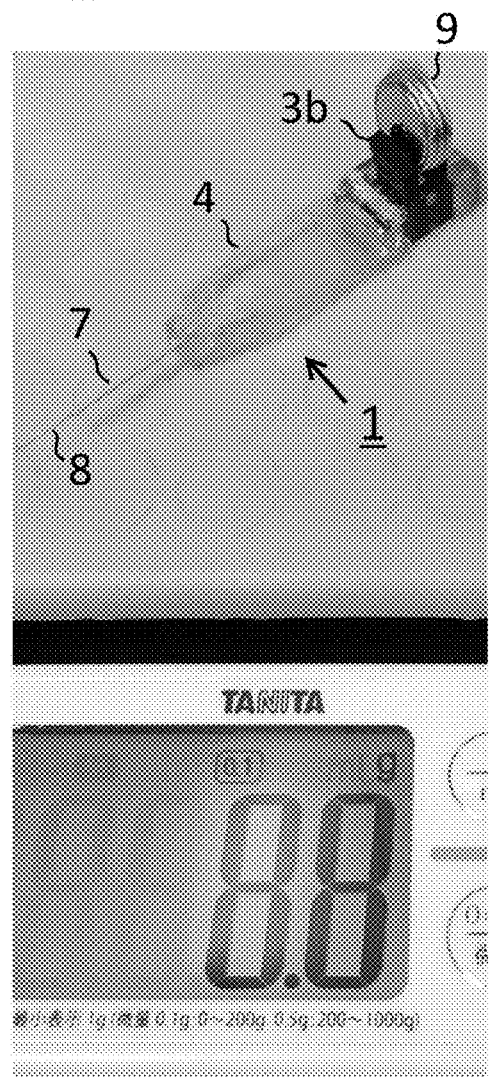

Further, the device produced in this example was proved to be an extremely light compact infusion device: the weight of the device containing the fluid and the liquid sample (which corresponds to the drug solution) was only 5.5 g, and even when the button cells were inserted, the total weight of the device was only 8.8 g. FIGS. 6A and 6B are the photographic images of the device.

INDUSTRIAL APPLICABILITY

The present invention is expected to be effectively applied in technical fields in which intravenous administration or subcutaneous injection is performed, such as the medical field and life science researches.

LIST OF REFERENCE NUMERALS

1: Compact infusion device
10: Fluid drive (electroosmotic pump)
20: Sandwiched structure
2: Porous body
21: Side surface of the porous body/flat side surface of the porous body/circular flat side surface of the porous body
3: Rubber electrode/rubber electrode containing electro-conductive material/rubber electrode containing carbon/rubber plate electrode
3a: Upstream rubber electrode
3b: Downstream rubber electrode
31: Communicating portion/communicating hole
32: Power supply support portion (structure for sandwiching and holding the power supply)/structure for supporting small batteries (structure for sandwiching and holding small batteries)
4: Support
5: Hollow structure/tubular hollow structure
50: Fluid holding portion (container-like structural body/bodies for holding the fluid)
51: Fluid supply reservoir
52: Opening
53: Fluid storage reservoir
54: Hole structure (communicating portion between the fluid storage reservoir and the drug solution holding channel)
55: Communicating structure (through-hole structure in the support into which the rubber electrode is inserted and fixed)
6: Drug solution holding channel
61: One-way valve
62: Curved tubular channel/continuously curved serpentine-shaped channel
63: Channel for installing the one-way valve
64: Drug solution introducing channel
65: Drug solution discharge channel
7: Needle holding portion/needle holding structure (structure to be connected to and hold the injection needle)/needle holding tube
8: Injection needle/extra-fine long needle
9: Power supply/small battery/button cell
11: Lid member/covering member
12: Stopper member

The invention claimed is:

1. A portable compact infusion device comprising:
   a fluid drive;
   a fluid holding portion;
   a drug solution holding channel; and
   a support,
   wherein (A) the fluid drive includes a porous body that allows generation of electroosmotic flow and a pair of rubber electrodes each containing electroconductive material and having a communicating portion, the porous body being sandwiched between the communicating portions of the pair of rubber electrodes to form a sandwiched structure;
   (B) the fluid holding portion includes a fluid supply reservoir spatially in contact with the communicating portion of one of the rubber electrodes in the sandwiched structure or connected to the communicating portion of the one of the rubber electrodes in the sandwiched structure through a member having a space or a channel; and
   (C) the drug solution holding channel is spatially in contact with the communicating portion of the other rubber electrode in the sandwiched structure or is connected to the communicating portion of the other rubber electrode in the sandwiched structure through a member having a space or a channel, and a part of the drug solution holding channel is directly or indirectly connectable to an injection needle.

2. The compact infusion device of claim 1,
   wherein (A') the fluid drive is operable as an electroosmotic flow pump; and
   (B') the fluid holding portion is a container-like structure/structures to hold fluid.

3. The compact infusion device of claim 1, wherein in the fluid drive,
   (a-1) the communicating portions of the pair of rubber electrodes in the sandwiched structure are substantially opposed to each other and sandwich the porous body in a manner in contact with the porous body;
   (a-2) the porous body is embedded in the support with a space provided at one side of each rubber electrode opposite to the porous body with respect to the communicating portion of each rubber electrode in the sandwiched structure; and
   (a-3) each of the rubber electrodes includes a protruding portion that protrudes from the support, and the protruding portions of the rubber electrodes are positioned to directly hold small batteries between the rubber electrodes.

4. The compact infusion device of claim 1, wherein the communicating portion of each rubber electrode includes a communicating hole, and the sandwiched structure includes a peripheral edge of the communicating hole of each rubber electrode partially or entirely in contact with the porous body.

5. The compact infusion device of claim 1,
   wherein the fluid drive generates a driving force that transports the fluid at a position nearer the fluid supply reservoir than the pair of rubber electrodes toward a position nearer the drug solution holding channel than the pair of rubber electrodes;
   the driving force is transmitted to transport a drug solution held inside the drug solution holding channel toward the injection needle; and
   infusion through the injection needle is performed without pulsation at flow rates of 1 to 50 nL/min.

6. The compact infusion device claim 1, wherein at least parts of the support in contact with the rubber electrodes are made of resin or rubber material.

7. The compact infusion device of claim 1, wherein the drug solution holding channel is substantially composed of a fine channel having a maximum channel width of 1 mm or less, and is configured to hold a drug solution of 0.01 to 4 mL.

8. The compact infusion device of claim 1, comprising the injection needle connected to or connectable to the compact infusion device.

9. The compact infusion device of claim 1, wherein the porous body is immersed in the fluid, and the fluid holding portion contains the fluid.

10. The compact infusion device of claim 1, wherein the total weight of the fluid drive, the fluid holding portion, the drug solution holding channel, and the support is 10 g or less.

* * * * *